(12) United States Patent
Weng et al.

(10) Patent No.: US 12,043,867 B2
(45) Date of Patent: Jul. 23, 2024

(54) COMPOSITIONS AND METHODS COMPRISING ASYMMETRIC BARCODING

(71) Applicant: AccuraGen Holdings Limited, George Town (KY)

(72) Inventors: Li Weng, Fremont, CA (US); Malek Faham, Burlingame, CA (US); Tobias Wittkop, San Mateo, CA (US)

(73) Assignee: ACCURAGEN HOLDINGS LIMITED, George Town (KY)

( * ) Notice: Subject to any disclaimer, the term of this patent is extended or adjusted under 35 U.S.C. 154(b) by 205 days.

(21) Appl. No.: 17/525,748

(22) Filed: Nov. 12, 2021

(65) Prior Publication Data

US 2022/0205032 A1   Jun. 30, 2022

Related U.S. Application Data

(63) Continuation of application No. 16/368,355, filed on Mar. 28, 2019, now Pat. No. 11,203,782.

(60) Provisional application No. 62/650,167, filed on Mar. 29, 2018.

(51) Int. Cl.
  *C12Q 1/6869* (2018.01)
  *C12Q 1/6806* (2018.01)

(52) U.S. Cl.
  CPC ......... *C12Q 1/6869* (2013.01); *C12Q 1/6806* (2013.01)

(58) Field of Classification Search
  CPC ... C12Q 1/6869; C12Q 1/6806; C12Q 1/6874
  See application file for complete search history.

(56) References Cited

U.S. PATENT DOCUMENTS

| | | | |
|---|---|---|---|
| 5,130,238 A | 7/1992 | Malek et al. |
| 5,234,809 A | 8/1993 | Boom et al. |
| 5,270,184 A | 12/1993 | Walker et al. |
| 5,310,652 A | 5/1994 | Gelfand et al. |
| 5,322,770 A | 6/1994 | Gelfand |
| 5,330,892 A | 7/1994 | Vogelstein et al. |
| 5,352,775 A | 10/1994 | Albertsen et al. |
| 5,362,623 A | 11/1994 | Vogelstein et al. |
| 5,399,491 A | 3/1995 | Kacian et al. |
| 5,455,166 A | 10/1995 | Walker |
| 5,480,784 A | 1/1996 | Kacian et al. |

(Continued)

FOREIGN PATENT DOCUMENTS

| CN | 101432439 A | 5/2009 |
|---|---|---|
| CN | 101935697 A | 1/2011 |

(Continued)

OTHER PUBLICATIONS

Bevan, et al., Sequencing of PCR-amplified DNA, PCR methods and applications, 1992; vol. 1: 222-228.

(Continued)

*Primary Examiner* — Samuel C Woolwine
*Assistant Examiner* — Lisa A. Horth
(74) *Attorney, Agent, or Firm* — WILSON SONSINI GOODRICH & ROSATI

(57) ABSTRACT

In some aspects, the present disclosure provides methods for identifying sequence variants, as well as methods of determining copy number of a genetic locus in a sample. Systems and kits for performing methods of the disclosure, as well as compositions produced by or useful in methods of the disclosure are also provided.

15 Claims, 5 Drawing Sheets

Variant not confirmed by both groups

Not reported as a variant

Variant confirmed by both groups

Reported as a variant

(56) References Cited

U.S. PATENT DOCUMENTS

| | | |
|---|---|---|
| 5,492,808 A | 2/1996 | De La Chapelle et al. |
| 5,527,670 A | 6/1996 | Stanley |
| 5,527,676 A | 6/1996 | Vogelstein et al. |
| 5,545,540 A | 8/1996 | Mian |
| 5,571,905 A | 11/1996 | Vogelstein et al. |
| 5,576,422 A | 11/1996 | Vogelstein et al. |
| 5,591,826 A | 1/1997 | Del La Chapelle et al. |
| 5,648,212 A | 7/1997 | Albertsen et al. |
| 5,691,454 A | 11/1997 | Albertsen et al. |
| 5,693,470 A | 12/1997 | De La Chapelle et al. |
| 5,693,536 A | 12/1997 | Vogelstein et al. |
| 5,705,628 A | 1/1998 | Hawkins |
| 5,783,666 A | 7/1998 | Albertsen et al. |
| 5,807,692 A | 9/1998 | Kinzler et al. |
| 5,830,676 A | 11/1998 | Vogelstein et al. |
| 5,837,443 A | 11/1998 | De La Chapelle et al. |
| 5,854,033 A | 12/1998 | Lizardi |
| 5,871,925 A | 2/1999 | De La Chapelle et al. |
| 5,871,968 A | 2/1999 | Kinzler et al. |
| 5,939,291 A | 8/1999 | Loewy et al. |
| 5,955,263 A | 9/1999 | Vogelstein et al. |
| 6,033,850 A | 3/2000 | Purvis |
| RE36,713 E | 5/2000 | Vogelstein et al. |
| 6,090,566 A | 7/2000 | Vogelstein et al. |
| 6,114,124 A | 9/2000 | Albertsen et al. |
| 6,156,504 A | 12/2000 | Gocke et al. |
| 6,210,891 B1 | 4/2001 | Nyren et al. |
| 6,245,515 B1 | 6/2001 | Vogelstein et al. |
| 6,251,639 B1 | 6/2001 | Kurn |
| 6,277,605 B1 | 8/2001 | Wijnhoven et al. |
| 6,300,059 B1 | 10/2001 | Vogelstein et al. |
| 6,333,157 B1 | 12/2001 | Miller-Jones et al. |
| 6,380,369 B1 | 4/2002 | Adams et al. |
| 6,410,278 B1 | 6/2002 | Notomi et al. |
| 6,413,727 B1 | 7/2002 | Albertsen et al. |
| 6,416,984 B1 | 7/2002 | Haseltine et al. |
| 6,482,606 B1 | 11/2002 | Adams et al. |
| 6,511,805 B1 | 1/2003 | Gocke et al. |
| 6,521,409 B1 | 2/2003 | Gocke et al. |
| 6,610,477 B1 | 8/2003 | Haseltine et al. |
| 6,620,619 B2 | 9/2003 | Haseltine et al. |
| 6,677,312 B1 | 1/2004 | Vogelstein et al. |
| 6,800,617 B1 | 10/2004 | Vogelstein et al. |
| 6,833,246 B2 | 12/2004 | Balasubramanian |
| 6,917,726 B2 | 7/2005 | Levene et al. |
| 6,939,675 B2 | 9/2005 | Gocke et al. |
| 6,946,251 B2 | 9/2005 | Kurn |
| RE38,916 E | 12/2005 | Vogelstein et al. |
| 6,977,148 B2 | 12/2005 | Dean et al. |
| 7,001,724 B1 | 2/2006 | Greenfield |
| 7,033,764 B2 | 4/2006 | Korlach et al. |
| 7,052,847 B2 | 5/2006 | Korlach et al. |
| 7,056,676 B2 | 6/2006 | Korlach et al. |
| 7,087,583 B2 | 8/2006 | Vogelstein et al. |
| 7,170,050 B2 | 1/2007 | Turner et al. |
| 7,183,053 B2 | 2/2007 | Gocke et al. |
| 7,208,275 B2 | 4/2007 | Gocke et al. |
| 7,267,955 B2 | 9/2007 | Vogelstein et al. |
| 7,282,335 B2 | 10/2007 | Gocke et al. |
| 7,288,380 B1 | 10/2007 | Gocke et al. |
| 7,326,778 B1 | 2/2008 | De La Chapelle et al. |
| 7,361,466 B2 | 4/2008 | Korlach et al. |
| 7,387,874 B2 | 6/2008 | Gocke et al. |
| 7,399,592 B2 | 7/2008 | Gocke et al. |
| 7,410,764 B2 | 8/2008 | Gocke et al. |
| 7,416,844 B2 | 8/2008 | Korlach et al. |
| 7,424,368 B2 | 9/2008 | Huang et al. |
| 7,537,897 B2 | 5/2009 | Brenner et al. |
| 7,569,349 B2 | 8/2009 | Gocke et al. |
| 7,569,350 B2 | 8/2009 | Gocke et al. |
| RE40,948 E | 10/2009 | Vogelstein et al. |
| 7,700,286 B2 | 4/2010 | Stroun et al. |
| RE41,327 E | 5/2010 | Gocke et al. |
| 7,790,395 B2 | 9/2010 | Gocke et al. |
| 7,824,890 B2 | 11/2010 | Hoser et al. |
| 7,935,484 B2 | 5/2011 | Gocke et al. |
| 7,935,487 B2 | 5/2011 | Gocke et al. |
| 7,972,817 B2 | 7/2011 | Kopreski |
| 8,048,629 B2 | 11/2011 | Gocke et al. |
| 8,209,130 B1 | 6/2012 | Kennedy et al. |
| 8,361,726 B2 | 1/2013 | Gocke et al. |
| RE44,596 E | 11/2013 | Stroun et al. |
| 8,835,358 B2 | 9/2014 | Fodor et al. |
| 8,916,351 B2 | 12/2014 | Murakami |
| 9,217,167 B2 | 12/2015 | Heller et al. |
| 9,260,753 B2 | 2/2016 | Xie et al. |
| 9,586,987 B2 | 3/2017 | Hayashizaki et al. |
| 10,155,980 B2 | 12/2018 | Weng et al. |
| 10,227,584 B2 | 3/2019 | Emerick et al. |
| 10,724,088 B2 | 7/2020 | Weng et al. |
| 10,752,942 B2 | 8/2020 | Weng et al. |
| 10,767,222 B2 | 9/2020 | Lin et al. |
| 11,203,782 B2 | 12/2021 | Weng et al. |
| 11,427,866 B2 | 8/2022 | Faham et al. |
| 11,578,359 B2 | 2/2023 | Weng et al. |
| 11,597,973 B2 | 3/2023 | Tang |
| 11,643,683 B2 | 5/2023 | Weng et al. |
| 2002/0042061 A1 | 4/2002 | Yang et al. |
| 2003/0100077 A1 | 5/2003 | Korte et al. |
| 2004/0058378 A1 | 3/2004 | Kong et al. |
| 2004/0067511 A1 | 4/2004 | Thomas |
| 2006/0228721 A1 | 10/2006 | Leamon et al. |
| 2007/0020646 A1 | 1/2007 | Hoon et al. |
| 2007/0087362 A1 | 4/2007 | Church et al. |
| 2007/0099208 A1 | 5/2007 | Drmanac et al. |
| 2007/0134128 A1 | 6/2007 | Korlach |
| 2008/0039417 A1 | 2/2008 | Wang et al. |
| 2009/0136924 A1 | 5/2009 | Larionov et al. |
| 2010/0304989 A1 | 12/2010 | Von Hoff et al. |
| 2011/0319299 A1 | 12/2011 | Osborne et al. |
| 2013/0217023 A1 | 8/2013 | Godwin et al. |
| 2013/0244885 A1 | 9/2013 | Wang et al. |
| 2013/0331288 A1 | 12/2013 | Gunderson et al. |
| 2014/0051154 A1 | 2/2014 | Hyland et al. |
| 2014/0066317 A1 | 3/2014 | Talasaz |
| 2014/0121116 A1 | 5/2014 | Richards et al. |
| 2014/0154683 A1 | 6/2014 | Vogelstein et al. |
| 2014/0221329 A1 | 8/2014 | Cronin et al. |
| 2014/0227705 A1 | 8/2014 | Vogelstein et al. |
| 2014/0234850 A1 | 8/2014 | Zhang et al. |
| 2014/0274740 A1 | 9/2014 | Srinivasan et al. |
| 2014/0296081 A1 | 10/2014 | Diehn et al. |
| 2014/0336236 A1 | 11/2014 | Cronin et al. |
| 2015/0031035 A1 | 1/2015 | Kvam et al. |
| 2015/0033372 A1 | 1/2015 | Bradley et al. |
| 2015/0044687 A1 | 2/2015 | Schmitt et al. |
| 2015/0141292 A1 | 5/2015 | Fodor et al. |
| 2015/0147815 A1 | 5/2015 | Babiarz et al. |
| 2015/0361492 A1 | 12/2015 | Vogelstein et al. |
| 2015/0366866 A1 | 12/2015 | Ali et al. |
| 2016/0040229 A1 | 2/2016 | Talasaz et al. |
| 2016/0145691 A1 | 5/2016 | Cronin et al. |
| 2016/0201135 A1 | 7/2016 | Cronin et al. |
| 2016/0319345 A1 | 11/2016 | Gnerre et al. |
| 2017/0204459 A1 | 7/2017 | Barany et al. |
| 2018/0363039 A1 | 12/2018 | Weng et al. |
| 2018/0363052 A1 | 12/2018 | Schmitt et al. |
| 2019/0323073 A1 | 10/2019 | Lin et al. |
| 2023/0167493 A1 | 6/2023 | Faham et al. |
| 2023/0287485 A1 | 9/2023 | Weng et al. |
| 2023/0357836 A1 | 11/2023 | Weng et al. |

FOREIGN PATENT DOCUMENTS

| | | |
|---|---|---|
| CN | 101985654 A | 3/2011 |
| CN | 102625850 A | 8/2012 |
| CN | 104745679 A | 7/2015 |
| EP | 0684315 A1 | 11/1995 |
| EP | 0390323 B1 | 12/1998 |
| EP | 0569527 B1 | 3/2001 |
| EP | 0730648 B1 | 8/2004 |
| EP | 2396430 B1 | 5/2013 |
| JP | 2004512134 A | 4/2004 |
| WO | WO-9844151 A1 | 10/1998 |

(56) References Cited

FOREIGN PATENT DOCUMENTS

| | | | |
|---|---|---|---|
| WO | WO-0049176 A1 | 8/2000 | |
| WO | WO-0055369 A1 | 9/2000 | |
| WO | WO-0118230 A1 | 3/2001 | |
| WO | WO-0138580 A2 | 5/2001 | |
| WO | WO-2007133703 A2 | 11/2007 | |
| WO | WO-2007140417 A2 | 12/2007 | |
| WO | WO-2007140417 A3 | 2/2008 | |
| WO | WO-2013074632 A1 | 5/2013 | |
| WO | WO-2013142389 A1 | 9/2013 | |
| WO | WO-2013181170 A1 | 12/2013 | |
| WO | WO-2014015084 A2 | 1/2014 | |
| WO | WO-2014039556 A1 | 3/2014 | |
| WO | WO-2015089333 A1 | 6/2015 | |
| WO | WO-2015100427 A1 | 7/2015 | |
| WO | WO-2016053638 A1 | 4/2016 | |
| WO | WO-2017062863 A1 * | 4/2017 | .............. C12Q 1/68 |
| WO | WO-2017201102 A1 | 11/2017 | |
| WO | WO-2018035170 A1 | 2/2018 | |

OTHER PUBLICATIONS

Co-pending U.S. Appl. No. 18/164,439, inventors Lin; Shengrong et al., filed Feb. 3, 2023.
Dean, et al. Rapid amplification of plasmid and phage DNA using phi29 DNA polymerase and multiply-primed rolling circle amplification. Genome Research 11.6 ( 2001): 1095-1099.
Dillon L.W. et al. Production of Extrachromosomal MicroDNAs Is Linked to Mismatch Repair Pathways and Transcriptional Activity. Cell Rep. Jun. 23, 2015;11(11):1749-59.
Faham M. et al. Deep-sequencing approach for minimal residual disease detection in acute lymphoblastic leukemia. Blood. Dec. 20, 2012;120(26):5173-80.
Huang, S.H. Inverse polymerase chain reaction. An efficient approach to cloning cDNA ends. Mol Biotechnol. Aug. 1994;2(1):15-22.
Jensen TJ et al., Noninvasive detection of a balanced fetal translocation from maternal plasma. Clin Chem. Oct. 2014;60(10):1298-305. Epub Jul. 16, 2014.
Kroenlein H. et al. Molecular analysis of the t(2;8)/MYC-IGK translocation in high-grade lymphoma/leukemia by long-distance inverse PCR. Genes Chromosomes Cancer. Mar. 2012;51(3):290-9.
Kumar et al. Normal and Cancerous Tissues Release Extrachromosomal Circular DNA (eccDNA) into the Circulation Mol Cancer Res 15(9):1197-1205 (2017).
Li et al. Isothermally sensitive detection of serum circulating miRNAs for lung cancer diagnosis. Anal Chem. Dec. 3, 2013;85(23):11174-9.
Liu W.H. et al. Inverse PCR-based RFLP scanning identifies low-level mutation signatures in colon cells and tumors. Cancer Res. Apr. 1, 2004;64(7):2544-51.
Mitchell, et al. Circulating MicroRNAs as Stable Blood-based Markers for Cancer Detection. Proceedings of the National Academy of Sciences of the United States of America. vol. 105, Issue. 30 (2008): pp. 10513-10518.
Mitsunobu et al.: Flap endonuclease activity of gene 6 exonuclease of bacteriophage T7. J Biol Chem. 289(9):5860-5875 doi:10.1074/jbc.M113.538611 (2014).
Nelson J.R. et al. TempliPhi, phi29 DNA polymerase based rolling circle amplification of templates for DNA sequencing. Biotechniques. Jun. 2002;Suppl:44-7. PMID: 12083397.
Ochman, et al. Genetic applications of an inverse polymerase chain reaction. Genetics. Nov. 1988;120(3):621-3.
Pavlopoulos A. Identification of DNA sequences that flank a known region by inverse PCR. Methods Mol Biol. 2011;772:267-75.
Schubert J. et al. Surveying cereal-infecting geminiviruses in Germany—diagnostics and direct sequencing using rolling circle amplification. Virus Res. Jul. 2007;127(1):61-70.
Shibata Y. et al. Extrachromosomal microDNAs and chromosomal microdeletions in normal tissues. Science. Apr. 6, 2012;336(6077):82-6. doi: 10.1126/science.1213307. Epub Mar. 8, 2012. Erratum in: Science. Jun. 22, 2012;336(6088):1506.
Tsaftaris A. et al. Rolling circle amplification of genomic templates for inverse PCR (RCA-GIP): a method for 5'-and 3'-genome walking without anchoring. Biotechnol Lett. Jan. 2010;32(1):157-61.
Zhang et al., "Amplification of target-specific, ligation-dependent circular probe" Gene (1998) 211:277-285.
Zhao et al.: Isothermal Amplification of Nucleic Acids. Chem Rev. 115(22):12491-12545 doi:10.1021/acs.chemrev.5b00428 (2015).
Amado, et al. Wild-type KRAS is required for panitumumab efficacy in patients with metastatic colorectal cancer. Journal of Clinical Oncology. Apr. 1, 2008; 26(10);1626-1634.
Awuah, et al. Thermal inactivation kinetics of trypsin at aseptic processing temperatures. Journal of food process engineering 1993 v.16 No. 4 pp. 315-328 (abstract).
Blast. Basic local alignment search tool. Available at http://blast.ncbi.nlm.nih.gov/Blast.cgi. Accessed on Oct. 10, 2016.
Bokemeyer, et al. Fluorouracil, leucovorin, and oxaliplatin with and without cetuximab in the first-line treatment of metastatic colorectal cancer. Journal of Clinical Oncology. Feb. 10, 2009; 27(5).: 663-671.
Dawson, et al., Analysis of circulating tumor DNA to monitor metastatic breast cancer. The New England Journal of Medicine. Mar. 28, 2013. 368(13); 1199-1209.
Delcher, et al. Alignment of whole genomes. Nucleic Acids Research. Feb. 2, 1999; 27(11): 2369-2376.
Dicker, et al. The detection of TP53 mutations in chronic lymphocytic leukemia independently predicts rapid disease progression and is highly correlated with a complex aberrant karyotype. Leukemia. Jan. 2009; 23(1):117-124.
Emboss. Emboss Water: Pairwise Sequence Alignment (NUCLEOTIDE). Available at http://www.ebi.ac.uk/Tools/psa/emboss_water/nucleotide.html. Accessed on Oct. 10, 2016.
Florsheim, et al. Integrated Innate Mechanisms Involved in Airway Allergic Inflammation to the Serine Protease Subtilisin. J Immunol. May 15, 2015; 194(10): 4621-4630.
Foss et al. Effects of fixative and fixation time on the extraction and polymerase chain reaction amplification of RNA from paraffin-embedded tissue. Comparison of two housekeeping gene mRNA controls. Diagn Mol Path 3:148-155 (1994).
Freshney. Culture of Animal Cells: A Manual of Basic Technique and Specialized Applications. 6th Edition. 2010.
Giacona, et al. Cell-free DNA in human blood plasma: length measurements in patients with pancreatic cancer and healthy controls. Pancreas. Jul. 1998;17(1):89-97.
Guatelli et al. Isothermal, in vitro amplification of nucleic acids by a multienzyme reaction modeled after retroviral replication. PNAS USA 87(5):1874-1878 (1990).
Harkins, et al., Replicating fetal trisomy patient-like reference material for use in non-invasive prenatal screening tests. Sera Care. AMP 2015. Nov. 5-7, 2015.
Harlow, et al. Antibodies: A Laboratory manual. Cold Spring Harbor Laboratory. 1988.
Heinrich. et al. Kinase mutations and imatinib response in patients with metastatic gastrointestinal stromal tumor. Journal of Clinical Oncology. Dec. 1, 2003; 21(23): 4342-4349.
Horizon Product Specification. cfDNA Reference Standard Set. 6068PSS-01(V-01). 2015.
Hussmann, et al. Reply to Schmitt et al.: Data-filtering schemes for avoiding double-counting in circle sequencing. PNAS. Apr. 22, 2014; 111(16).
Illumina. Genome Analyzer System. Available at http://support.illumina.com/content/dam/illumina-marketing/documents/products/datasheets/datasheet_genome_analyzeriix.pdf. Accessed onOct. 10, 2016.
Jeffreys et al. DNA Enrichment by Allele-Specific Hybridization (DEASH): A Novel Method for Haplotyping and for Detecting Low-Frequency Base Substitutional Variants and Recombinant DNA Molecules. Genome Research 13:2316-2324 (2003).
Katayama, et al. Mechanisms of acquired crizotinib resistance in ALK-rearranged lung cancers. Sci. Transl Med. Feb. 8, 2012; 8(4).
Kent, W.J. Blat—The Blast-like alignment tool. Genome Research. 2002: 656-664.
Kurtz, et al. Versatile and open software for comparing large genomes. Biomed central. Jan. 30, 2004.

(56) References Cited

OTHER PUBLICATIONS

Landegren, U. Molecular mechanics of nucleic acid sequence amplification. Elsevier Science. Jun. 1993. 9(6). 199-204.
Langmead et al. Ultrafast and memory-efficient alignment of short DNA sequences to the human genome. Genome biology 10:R25 (10 pgs) (2009).
Larking, et al. Clustal W and Clustal X version 2.0. Bioinformatics applications note. 2007. 2947-2948; 23(21).
Lee, et al. Nucleic acid amplification technologies: application to disease diagnosis. Biotechniques books. 1997.
Li, et al. Fast and accurate long-read alignment with burrows-wheeler transform. Bioinformatics. 2010. Mar. 1;26(5):589-95.
Li, et al. Fast and accurate short read alignment with Burrows-Wheeler transform. Bioinformatics. Jul. 15, 2009;25(14):1754-1760. doi: 10.1093/bioinformatics/btp324. Epub May 18, 2009.
Li, et al. Technical advance: Whole genome amplification of plasma-circulating DNA enables expanded screening for allelic imbalance in plasma. Journal of Molecular Diagnostics. Feb. 2006. 8(1); 22-30.
Lin, et al. Rolling Circle Enzymatic Replication of a Complex Multi-Crossover DNA Nanostructure. J Am Chem Soc. Nov. 21, 2007; 129(46): 14475-14481.
Lipman, et al. Rapid and sensitive protein similarity searches. Science. Mar. 22, 1985; 227(4693):1435-41.
Lizardi, et al. Exponential amplification of recombinant-RNA hybridization probes. Biotechnology. 1988. 6:1197-1202.
Lou, et al. High-throughput DNA sequencing errors are reduced by orders of magnitude using circle sequencing. Proc Natl Acad Sci U S A. Dec. 3, 2013;110(49):19872-7. doi: 10.1073/pnas.1319590110. Epub Nov. 15, 2013.
Lou et al., Supporting Information for "High-throughput DNA sequencing errors are reduced by orders of magnitude using circle sequencing," Proc Natl Acad Sci U S A., 110(49):19872-7. doi: 10.1073/pnas.1319590110 (14 pages) (2013).
Lou et al. BioTechniques, pp. 1-14 [Support Information to Lou et al. BioTechniques 110(49) publication] (2013).
Maldonado, et al. Determinants of BRAF mutations in primary melanomas. Journal of the National Cancer Institute. Dec. 17, 2003; 95(24):1878-1890.
Matta, et al. Isolation and partial characterization of a thermostable extracellular protease of Bacillus polymyxa B-17. Int J Food Microbiol. Jul. 21, 1998;42(3):139-45 (abstract).
McLendon, et al. Survival analysis of presumptive prognostic markers among oligodendrogliomas. John Wiley & Sons. Oct. 15, 2005; 104(8):1693-1699.
McPherson, M. J. et al.(Eds.) PCR 2: A Practical Approach. Practical approach series. IRL Press. 1995. (Table of Contents).
Miller, et al. A simple salting out procedure for extracting DNA from human nucleated cells. Nucleic Acid Research. 1988; 16(3).
Misale, et al. Emergence of KRAS mutations and acquired resistance to anti-EGFR therapy in colorectal cancer. Nature. Jun. 13, 2012; 486(7404):532-536.
Neumann, et al., Frequency and type of KRAS mutations in routine diagnostic analysis of metastatic colorectal cancer. Pathol Res Pract. 2009;205(12):858-62.
Newman, et al. An ultrasensitive method for quantitating circulating tumor DNA with broad patient coverage. Nat Med. May 2014;20(5):548-54. Epub Apr. 6, 2014.
Novocraft Technologies SDN BHD. NovoAlign. Available at http://www.novocraft.com/products/novoalign/. Accessed on Oct. 10, 2016.
Olivier, et al., TP53 mutations in human cancers: origins, consequences, and clinical use. Cold Spring Harb. Perspect Biology. 2010;1-17.
Pao, et al., EGF receptor gene mutations are common in lung cancers from "never smokers" and are associated with sensitivity of tumors to gefitinib and erlotinib. Proc. Natl. Acad. Sci. USA. Sep. 7, 2004; 101(36):13306-13311.
Paska et al. Effect of formalin, acetone, and RNAlater fixatives on tissue preservation and different size amplicons by real-time PCR from paraffin-embedded tissue. Diagn Mol Path 13(4):234-240 (2004).
Pearson et al. Improved Tools for Biological Sequence Comparison. Pnas USA 85:2444-48 (1988).
Polidoros, et al., Rolling circle amplification-RACE: A method for simultaneous isolation of 5' and 3' cDNA ends from amplified cDNA templates. BioTechniques 41.1 (Jul. 2006):35-42. including p. 1/1 of Supplementary Material.
Promega. Thermolysin—Thermostable Proteinase with High Digest Temperature; Better Denaturation, Digestion of Proteolytically Resistant Proteins. Available at https://www.promega.com/products/mass-spectrometry/proteases-and-surfactants/thermolysin/. Accessed Apr. 11, 2018.
Qiagen. How can QIAGEN Protease and Proteinase K be inactivated? Available at https://www.qiagen.com/ca/resources/faq?id=d24681d7-88e7-421a-84d9-27bfd5141103&lang=en. Accessed Apr. 11, 2018.
Remacle, et al. Substrate Cleavage Analysis of Furin and Related Proprotein Convertases—A Comparative Study. J Biol Chem. Jul. 25, 2008; 283(30): 20897-20906.
Samuels, et al. High Frequency of Mutations of the PIK3CA Gene in Human Cancers. Science Mag. Apr. 23, 2004; 304.
Schmitt, et al. Risks of double-counting in deep sequencing. PNAS. Apr. 22, 2014;111(16).
Shaw, et al. Clinical Features and Outcome of Patients With Non-Small-Cell Lung Cancer Who Harbor EML4-ALK. Journal of Clinical Oncology. Sep. 10, 2009; 27(26):4247-4253.
Sievers, et al. Fast, Scalable generation of high-quality protein multiple sequence alignments using clustal omega. Molecular systems biology. 2011.
Sigma-Aldrich. Protease from Streptomyces griseus. Available at https://www.sigmaaldrich.com/catalog/product/sigma/p6911?lang=en®ion=US#. Accessed Apr. 11, 2018.
Slater, et al. Automated generation of heuristics for biological sequence comparison. BMC Bioinformatics. Feb. 15, 2005; 6(31): 1-11.
SOAP.Short Oligonucleotide Analysis Package. Available at http://soap.genomics.org.cn/. Accessed on Oct. 10, 2016.
Sourceforge-Maq-Mapping-and-Assembly-with-Qualities. Available at http://maq.sourceforge.net/. Accessed on Oct. 10, 2016.
Stanford. HIV Drug resistance database. Available at https://hivdb.stanford.edu/pages/genotype-rx.html. Accessed on Oct. 10, 2016.
Tissen, P. Laboratory techniques in biochemistry and molecular biology: Hybridization with nucleic acid probes. Elsevier Science. 1993.
Walsh, et al. Chelex 100 as a medium for simple extraction of DNA for PCR-based typing from forensic material. BioTechniques. 1991;10(4):506-513.
Mo et al., Cell-free Circulating miRNA Biomarkers in Cancer. Journal of Cancer, 3:432-448 (2012).
Snyder et al., Cell-free DNA comprises an in vivo nucleosome footprint that informs its tissues-of-origin. Cell 164(1-2):57-68 (Jan. 14, 2016) https://doi.org/10.1016/j.cell.2015.11.050.
Travers et al., A flexible and efficient template format for circular consensus sequencing and SNP detection. Nucleic Acids Research 38(15):e159 (2010) https://doi.org/10.1093/nar/gkq543.

* cited by examiner

COMPOSITIONS AND METHODS COMPRISING ASYMMETRIC BARCODING

CROSS REFERENCE TO RELATED APPLICATIONS

This application is a continuation of U.S. Ser. No. 16/368,355, filed Mar. 28, 2019, which claims the benefit of priority to U.S. Provisional Patent Application No. 62/650,167, filed Mar. 29, 2018, which are hereby incorporated by reference in their entirety.

BACKGROUND

"Deep" sequencing of cell-free nucleic acids in clinical samples to identify rare variant sequences has made a significant impact on clinical science and medicine in general. However, distinguishing genuine sequence variants from sequencing, amplification and/or other processing errors remains a central challenge associated with sequence-based assays. This challenge has been addressed in several ways including, for example, by technology improvements that increase next-generation sequencing (NGS) read accuracy and by increasing the number of templates sequenced at each locus for improved error analysis. In spite of such advances, further improvements are still required, particularly in circumstances where the size of patient samples is severely limited.

SUMMARY

In view of the foregoing, there is a need for sequencing methods having higher accuracy and an ability to detect mutations that occur at lower frequency in a population. The present disclosure addresses these needs, and provides additional advantages as well. In some aspects, the present disclosure provides methods and compositions for identifying rare sequence variants at one or more genetic loci and for measuring copy number variations at one or more genetic loci. Aspects of the present disclosure are exemplified in a number of implementations and applications, some of which are summarized below and throughout the specification.

The present disclosure provides methods of identifying complementary strands of a double-stranded polynucleotide. In an aspect, a method of identifying complementary strands of a double-stranded polynucleotide comprises (a) subjecting a sense strand circular polynucleotide and an antisense strand circular polynucleotide originating from a double-stranded polynucleotide to a rolling circle amplification reaction using (i) a sense strand primer comprising a sense strand identifying barcode, and (ii) an antisense strand primer comprising an antisense strand identifying barcode, wherein the rolling circle amplification reaction yields barcoded concatemers, each comprising a junction sequence formed at a circularization junction of a circular polynucleotide and multiple repeats of the circular polynucleotide sequence; (b) subjecting the barcoded concatemers to a primer extension reaction using a first set and a second set of auxiliary primers to generate a plurality of amplicons, wherein the first set of auxiliary primers hybridize to a barcoded concatemer of the sense strand and the second set of auxiliary primers hybridize to a barcoded concatemer of the antisense strand, individual primers of the first set and the second set of auxiliary primers are distinctly barcoded with respect to other members of the same set, and wherein individual amplicons generated are distinguishable from each other by a unique combination of (i) the strand identifying barcode at one end and (ii) a distinct auxiliary barcode at the other end; (c) sequencing the amplicons or derivatives thereof to produce sequencing reads; and (d) identifying the sense strand and the antisense strand as complementary strands of the double-stranded polynucleotide from the sequencing reads based on (i) junction sequence and (ii) the sense strand identifying barcode and antisense strand identifying barcode.

In some embodiments, the sense strand circular polynucleotide and the antisense strand circular polynucleotide are generated by (i) forming single-stranded polynucleotides from the double-stranded polynucleotide, and (ii) subjecting the single-stranded polynucleotides to a ligation reaction. In some embodiments, the sense strand circular polynucleotide and the antisense strand circular polynucleotide are generated by (i) subjecting the double-stranded polynucleotide to a ligation reaction to yield a double-stranded, circular polynucleotide, and (ii) forming single-stranded, circular polynucleotides from the double-stranded, circular polynucleotide. In some embodiments, barcoded concatemers in (a) comprise two or more repeats of the circular polynucleotide sequence.

In some embodiments, the sense strand primer and/or the anti sense strand primer comprises a gene specific sequence. In some embodiments, primers of the first set and/or the second set of auxiliary primers comprise gene specific primer sequences. In some embodiments, the sense strand primer and/or the antisense strand primer further comprises a tag sequence, a sequencing primer binding sequence, or both. In some embodiments, primers of the first set and/or the second set of auxiliary primers further comprise a tag sequence, a sequencing primer binding sequence, or both.

The present disclosure provides methods of identifying a sequence variant in a polynucleotide, for example a polynucleotide in a nucleic acid sample. In an aspect, a method of identifying a sequence variant in a polynucleotide relative to a reference sequence comprises (a) subjecting a sense strand circular polynucleotide and an antisense strand circular polynucleotide originating from a double-stranded polynucleotide to a rolling circle amplification reaction using (i) a sense strand primer comprising a sense strand identifying barcode, and (ii) an antisense strand primer comprising an antisense strand identifying barcode, wherein the rolling circle amplification reaction yields barcoded concatemers, each comprising a junction sequence formed at a circularization junction of a circular polynucleotide and multiple repeats of the circular polynucleotide sequence; (b) subjecting the barcoded concatemers to a primer extension reaction using a first set and a second set of auxiliary primers to generate a plurality of amplicons, wherein the first set of auxiliary primers hybridize to a barcoded concatemer of the sense strand and the second set of auxiliary primers hybridize to a barcoded concatemer of the antisense strand, individual primers of the first set and the second set of auxiliary primers are distinctly barcoded with respect to other members of the same set, and wherein individual amplicons generated are distinguishable from each other by a unique combination of (i) the strand identifying barcode at one end and (ii) a distinct auxiliary barcode at the other end; (c) sequencing the amplicons or derivatives thereof to produce sequencing reads; and (d) calling a sequence difference as a sequence variant relative to a reference sequence when the sequence difference occurs in (i) sequencing reads sharing the same junction sequence, (ii) sequence reads having different strand-identifying barcodes, and (iii) sequence reads having the same strand identifying barcodes but different auxiliary barcodes.

In an aspect, a method of identifying a sequence variant in a polynucleotide relative to a reference sequence comprises (a) subjecting sense strand circular polynucleotides and antisense strand circular polynucleotides to a rolling circle amplification reaction using (i) sense strand primers comprising a sense strand identifying barcode and (ii) antisense strand primers comprising an antisense strand identifying barcode, wherein the rolling circle amplification reaction yields barcoded concatemers, each comprising a junction sequence formed at a circularization junction of a circular polynucleotide and multiple repeats of the circular polynucleotide sequence; (b) subjecting the barcoded concatemers to a primer extension reaction using a first set and a second set of auxiliary primers to generate a plurality of amplicons, wherein the first set of auxiliary primers hybridize to a barcoded concatemer of a sense strand and the second set of auxiliary primers hybridize to a barcoded concatemer of an anti-sense strand, individual primers of the first set and the second set of auxiliary primers are distinctly barcoded with respect to other members of the same set, and wherein individual amplicons generated are distinguishable from each other by a unique combination of (i) the strand identifying barcode at one end and (ii) a distinct auxiliary barcode at the other end; (c) sequencing the amplicons or derivatives thereof to produce sequencing reads; and (d) calling a sequence difference in a sense strand or an antisense strand relative to a reference sequence as a sequence variant when the sequence difference occurs in sequencing reads having a different junction sequence.

In some embodiments, prior to (d), sequencing reads are grouped into amplicon families, wherein an amplicon family comprises sequencing reads having the same strand identifying barcode, the same auxiliary barcode, and the same junction sequence. In some embodiments, a given sequencing read is identified as having the sequence difference when the sequence difference occurs in at least 50% of repeats in the given sequencing read. In some embodiments, a given amplicon family is identified as having the sequence difference when the sequence difference occurs in at least 70% of sequencing reads in the amplicon family.

In some embodiments, in (d), the sequence difference in the sense strand or antisense strand relative to the reference sequence is called a true sequence difference when the sequence difference occurs in at least 50% of amplicon families corresponding to the sense strand or antisense strand.

In some embodiments, the sense strand circular polynucleotide and the antisense strand circular polynucleotide are generated by (i) forming single-stranded polynucleotides from a double-stranded polynucleotide, and (ii) subjecting the single-stranded polynucleotides to a ligation reaction. In some embodiments, the sense strand circular polynucleotide and the antisense strand circular polynucleotideare generated by (i) subjecting a double-stranded polynucleotide to a ligation reaction to yield double-stranded, circular polynucleotides, and (ii) forming single-stranded, circular polynucleotides from the double-stranded, circular polynucleotide. In some embodiments, barcoded concatemers in (b) comprise two or more repeats of the circular polynucleotide sequence.

In some embodiments, the sense strand primer and/or the antisense primer comprises a gene specific sequence. In some embodiments, primers of the first set and/or the second set of auxiliary primers comprise gene specific sequences. In some embodiments, the sense strand primer and/or the antisense strand primer further comprise a tag sequence, a sequencing primer binding sequence, or both. In some embodiments, primers of the first set and/or the second set of auxiliary primers further comprise a tag sequence, a sequencing primer binding sequence, or both.

The present disclosure provides methods of identifying copy number variation. In an aspect, a method of identifying a copy number variation of a genetic locus in a sample comprises (a) subjecting sense strand circular polynucleotides and antisense strand circular polynucleotides to a rolling circle amplification reaction using (i) sense strand primers comprising a sense strand identifying barcode and (ii) antisense strand primers comprising an antisense strand identifying barcode, wherein the rolling circle amplification reaction yields barcoded concatemers, each comprising a junction sequence formed at a circularization junction of a circular polynucleotide and multiple repeats of the circular polynucleotide sequence; (b) subjecting the barcoded concatemers to a primer extension reaction using a first set and a second set of auxiliary primers to generate amplicons, wherein the first set of auxiliary primers hybridize to a barcoded concatemer of a sense strand and the second set of auxiliary primers hybridize to a barcoded concatemer of an antisense strand, individual primers of the first and the second set of auxiliary primers are distinctly barcoded with respect to other members of the same set, and wherein individual amplicons generated are distinguishable from each other by a unique combination of (i) the strand identifying barcode at one end and (ii) a distinct auxiliary barcode at the other end; (c) sequencing the amplicons or derivatives thereof to produce sequencing reads; (d) identifying one or more distinct polynucleotides comprising the genetic locus as originating from distinct single-stranded target polynucleotides via (i) a distinct junction sequence or (ii) the strand identifying barcode; and (e) identifying a copy number variation of the genetic locus when the number of distinct polynucleotides comprising the genetic locus, when compared to a number of distinct polynucleotides comprising a reference region, indicates a copy number variation of the genetic locus.

In some embodiments, prior to (d), sequencing reads are grouped into amplicon families, wherein an amplicon family comprises sequencing reads having the same strand identifying barcode, the same auxiliary barcode, and the same junction sequence.

In some embodiments, sense strand circular polynucleotides and antisense strand circular polynucleotides are generated by (i) forming single-stranded polynucleotides from double-stranded polynucleotides, and (ii) subjecting the single-stranded polynucleotides to a ligation reaction. In some embodiments, sense strand circular polynucleotides and antisense strand circular polynucleotides are generated by (i) subjecting double-stranded polynucleotides to a ligation reaction to yield double-stranded, circular polynucleotides, and (ii) forming single-stranded, circular polynucleotides from the double-stranded, circular polynucleotides. In some embodiments, barcoded concatemers in (b) comprise two or more repeats of the circular polynucleotide sequence.

In some embodiments, the sense strand primers and/or the anti-sense primers comprise a gene specific sequence. In some embodiments, primers of the first set and/or the second set of auxiliary primers comprise gene specific sequences. In some embodiments, the sense strand primer and/or the anti-sense strand primer further comprise a tag sequence, a sequencing primer binding sequence, or both. In some embodiments, primers of the first set and/or the second set of auxiliary primers further comprise a tag sequence, a sequencing primer binding sequence, or both.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1A:
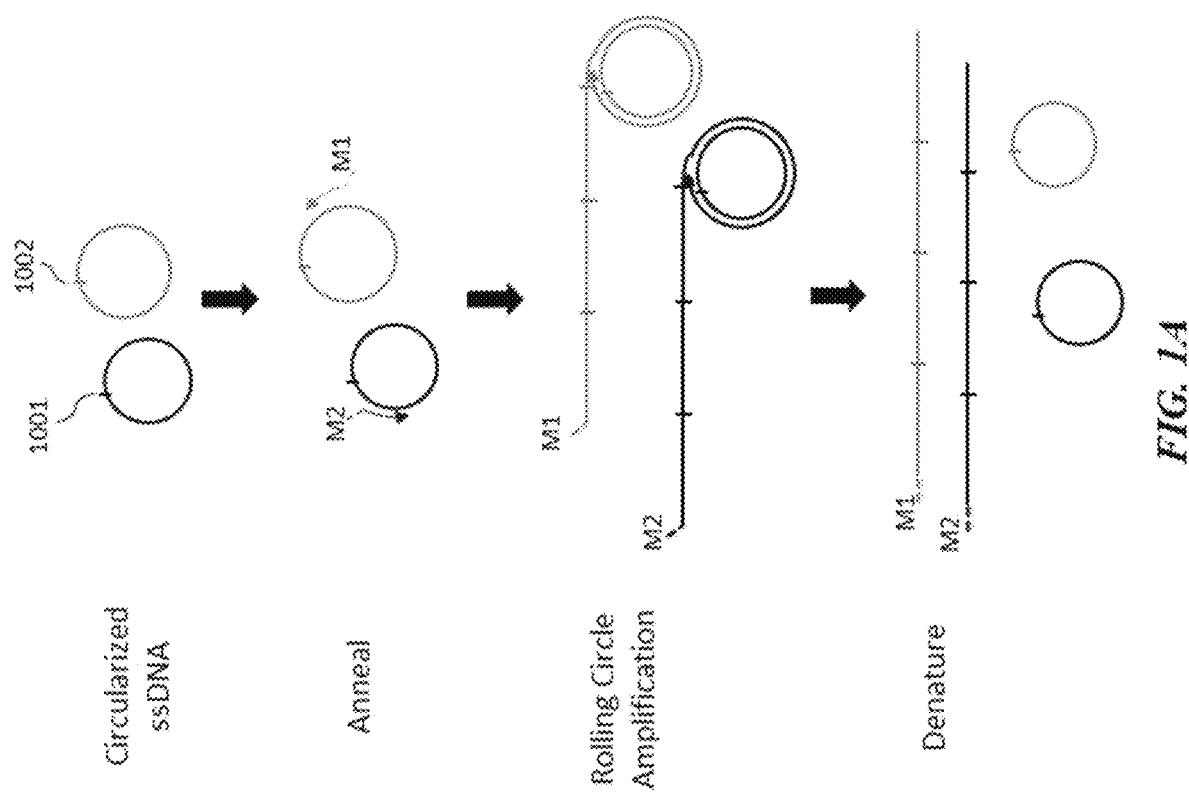
FIGS. 1A and 1B illustrate an example method of generating amplicons.

The practice of the various aspects and embodiments of the present disclosure may employ, unless otherwise indicated, conventional techniques and descriptions of organic chemistry, molecular biology (including recombinant techniques), cell biology, and biochemistry, which are within the skill of the art. Such conventional techniques include, but are not limited to, preparation and use of synthetic peptides, synthetic polynucleotides, monoclonal antibodies, nucleic acid cloning, amplifying, sequencing and analysis, and related techniques. Specific illustrations of suitable techniques are provided in the examples provided herein. However, other equivalent conventional procedures can also be used. Such conventional techniques and descriptions can be found in standard laboratory manuals such as *Genome Analysis: A Laboratory Manual Series* (Vols. I-IV); *PCR Primer: A Laboratory Manual; and Molecular Cloning: A Laboratory Manual* (all from Cold Spring Harbor Laboratory Press); Lutz and Bornscheuer, Editors, Protein Engineering Handbook (Wiley-VCH, 2009); Hermanson, Bioconjugate Techniques, Second Edition (Academic Press, 2008); and like references.

Unless otherwise specifically defined herein, terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); and Strachan and Read, Human Molecular Genetics, Second Edition (Wiley-Liss, New York, 1999).

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, for example within 5-fold or within 2-fold of a value. Where particular values are described in the application and claims, unless otherwise stated the term "about" meaning within an acceptable error range for the particular value should be assumed.

The terms "polynucleotide," "nucleic acid," and "oligonucleotide" are used interchangeably. As used herein, they generally refer to a polymeric form of nucleotides of any length, either deoxyribonucleotides or ribonucleotides, or analogs thereof. Polynucleotides may have any three dimensional structure, and may perform any function, known or unknown. Non-limiting examples of polynucleotides are coding or non-coding regions of a gene or gene fragment, intergenic DNA, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), small nucleolar RNA, ribozymes, cDNA, recombinant polynucleotides, branched polynucleotides, plasmids, vectors, isolated DNA of any sequence, isolated RNA of any sequence, nucleic acid probes, adapters, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

A polynucleotide may have a 5' end and 3' end, referring to the end-to-end chemical orientation of a single-strand of polynucleotide or nucleic acid. In a single-strand of linear DNA or RNA, the chemical convention of naming carbon atoms in the nucleotide sugar-ring means that there generally exists a 5' end which frequently contains a phosphate group attached to the 5' carbon and a 3' end which typically is unmodified from the ribose —OH substituent (hydroxyl group). In some cases, a polynucleotide may have a —OH substituent or a hydroxyl group at a 5' end and —P group or phosphate group at a 3' end. A phosphate group attached to the 5'-end permits ligation of two nucleotides, e.g., the covalent binding of a 5'-phosphate to the 3'-hydroxyl group of another nucleotide, to form a phosphodiester bond. Removal of the 5'-phosphate may inhibit or prevent ligation. The 3'-hydroxyl group is also important as it is joined to the 5'-phosphate in ligation.

The term "strand" is also used herein to refer to a polynucleotide, nucleic acid, or oligonucleotide. Polynucleotides can occur in "single-stranded" form or "double-stranded form." In double-stranded form, two polynucleotide strands can be hybridized as a result of sequence complementarity. Two strands of a double-stranded polynucleotide may have complementary sequences but the two strands can be distinguished from one another by sequence, when read in a 5' to 3' direction. The two strands may be referred to as the "top" and "bottom" strands, the "first" and "second" strands, the "first complementary" and the "second complementary" strands, the "coding" and "noncoding" strands, the "Watson" and "Crick" strands, or the "sense" and "antisense" strands.

The terms "hybridize," "hybridization," "hybridizing," "anneal," and "annealing," as used herein, generally refer to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR, or the enzymatic cleavage of a polynucleotide by a ribozyme.

A first sequence that can be stabilized via hydrogen bonding with the bases of the nucleotide residues of a second sequence is said to be "hybridizable" to the second sequence. In such a case, the second sequence can also be said to be hybridizable to the first sequence.

The terms "complement," "complements," "complementary," and "complementarity," as used herein, generally refer to a sequence that is fully complementary to and hybridizable to a given sequence. In some cases, a sequence hybridized with a given nucleic acid is referred to as the "complement" or "reverse-complement" of the given molecule if its sequence of bases over a given region is capable of complementarily binding those of its binding partner, such that, for example, A-T, A-U, G-C, and G-U base pairs are formed. In general, a first sequence that is hybridizable to a second sequence is specifically or selectively hybridizable to the second sequence, such that hybridization to the second sequence or set of second sequences is preferred (e.g. thermodynamically more stable under a given set of conditions, such as stringent conditions commonly used in the art) to hybridization with non-target sequences during a hybridization reaction. Typically, hybridizable sequences share a degree of sequence complementarity over all or a portion of their respective lengths, such as between 25%-100% complementarity, including at least 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, and 100% sequence complementarity. Sequence identity, such as for the purpose of assessing percent complementarity, may be measured by any suitable alignment algorithm, including but not limited to the Needleman-Wunsch algorithm (see e.g. the EMBOSS Needle aligner available at www.ebi.ac.uk/Tools/psa/emboss needle/nucleotide.html, optionally with default settings), the BLAST algorithm (see e.g. the BLAST alignment tool available at blast.ncbi.nlm.nih.gov/Blast.cgi, optionally with default settings), or the Smith-Waterman algorithm (see e.g. the EMBOSS Water aligner available at www.ebi.ac.uk/Tools/psa/emboss water/nucleotide.html, optionally with default settings). Optimal alignment may be assessed using any suitable parameters of a chosen algorithm, including default parameters.

The term "target polynucleotide" refers to a nucleic acid molecule or polynucleotide in a sample of nucleic acid molecules having a target sequence whose presence, amount, and/or nucleotide sequence, or changes in one or more of these, are desired to be determined. The target polynucleotide may be a portion of a larger polynucleotide (e.g. a portion to be amplified, sequenced, or otherwise analyzed), or may be used to refer to the larger polynucleotide comprising a target sequence. In general, the term "target sequence" refers to a nucleic acid sequence on a single strand of nucleic acid. The target sequence may be a portion of a gene, a regulatory sequence, genomic DNA, cDNA, fusion gene, RNA including mRNA, miRNA, rRNA, or others. The target sequence may be a target sequence from a sample or a secondary target such as a product of an amplification reaction.

The terms "ligate" and "ligation," as used herein, refer to any enzymatic or non-enzymatic process by which an inter-nucleotide linkage is formed between two polynucleotide ends. For example, the ends of DNA fragments can be ligated by forming a phosphodiester bond between the 3'-hydroxyl of one DNA terminus with the 5'-phosphoryl of another. In some cases, the inter-nucleotide linkage can be formed between two polynucleotide fragments (intermolecular). In some cases, the inter-nucleotide linkage can be formed between two terminal ends (5' end and 3' end) of a single fragment (intramolecular). Terminal ends of RNA fragments can similarly be joined by the formation of a phosphodiester bond. Polynucleotides that can be ligated may either be single-stranded or double-stranded. Double-stranded nucleic acids can comprise staggered ends, overhangs, or sticky ends where there are unpaired nucleotides at the 3' or 5' end of the DNA or RNA molecule. Double-stranded nucleic acids can comprise blunt ends, where the end nucleotides are paired at the 3' or 5' end of the DNA or RNA molecule. Ligation can comprise use of an enzyme, such as a ligase enzyme.

"Amplify," "amplifies," "amplified," "amplification," as used herein, generally refer to any process by which one or more copies are made of a target polynucleotide or a portion thereof. A variety of methods of amplifying polynucleotides (e.g. DNA and/or RNA) are available, some examples of which are described herein. Amplification may be linear, exponential, or involve both linear and exponential phases in a multi-phase amplification process. Amplification methods may involve changes in temperature, such as a heat denaturation step, or may be isothermal processes that do not require heat denaturation.

In general, the term "primer" refers to an oligonucleotide, either natural or synthetic, that is capable of, upon forming a duplex with a polynucleotide template, acting as a point of initiation of nucleic acid synthesis and being extended from its 3' end along the template so that an extended duplex is formed. The sequence of nucleotides added during the extension process may be determined by the sequence of the template polynucleotide. Primers can be extended by polymerases, for example DNA polymerase. Primers usually have a length in the range of from 5 to 36 nucleotides, but can be longer than 36 nucleotides or shorter than 5 nucleotides.

"Rolling circle amplification" or "RCA" refer to a process in which a primer is annealed to a circular nucleic acid molecule and extended by a nucleic acid polymerase in the presence of nucleoside triphosphates to produce an extension product that contains one or more copies (e.g., repeats), and usually a plurality of copies, of the complementary sequence of the circular DNA molecule.

"Concatemer," as used herein, generally refers to a ligation product or an amplification product comprising a continuous polynucleotide that in one embodiment contains more than one copy (e.g., repeat) of a target polynucleotide sequence (e.g. more than 1, 2, 3, 4, 5, 6, 7, 8, 9, or 10 repeats of the target sequence). In some embodiments, a concatemer comprises at least 2 copies of a target polynucleotide sequence. In some embodiments, a concatemer contains multiple copies, or a plurality of copies, of a target polynucleotide sequence linked in tandem. In some embodiments, additional polynucleotide sequences are interspersed between the multiple copies, or plurality of copies, of a target polynucleotide sequence. For example, a barcode sequence may be interspersed between the copies of the target polynucleotide sequence.

"Genetic locus," or "locus" in reference to a genome or target polynucleotide, refers to a contiguous sub-region or segment of the genome or target polynucleotide. As used herein, genetic locus, or locus, may refer to the position of a nucleotide, a gene, or a portion of a gene in a genome, including mitochondrial DNA, or it may refer to any contiguous portion of genomic sequence whether or not it is within, or associated with, a gene. In some embodiments, a genetic locus refers to any portion of genomic sequence, including mitochondrial DNA, from a single nucleotide to a segment of few hundred nucleotides, e.g. about 100-300, in length. In other embodiments, a genetic locus refers to any portion of genomic sequence from a single nucleotide to a segment of a few tens of nucleotides, e.g. about 10-30, in length. In some embodiments, a particular genetic locus may be identified by its nucleotide sequence, or the nucleotide sequence, or sequences, of one or both adjacent or flanking regions. In some embodiments, a genetic locus may be a single nucleotide position. In some embodiments, a genetic locus comprises a sequence variant, or equivalently, a genetic variant. In such embodiments, a genetic variant at the genetic locus may be a nucleotide at the position of the genetic locus, which nucleotide occurs naturally in a population and which may be referred to as a single nucleotide polymorphism, or as an allele. In other embodiments, a genetic locus may comprise an insertion of one or more nucleotides or a deletion of one or more nucleotides with respect to a reference sequence.

In general, the term "kit" refers to any delivery system for delivering materials or reagents for carrying out a method of the present disclosure. In the context of reaction assays, such delivery systems include systems that allow for the storage, transport, or delivery of reaction reagents (e.g., primers, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second container contains primers.

"Barcode," as used herein, refers to an oligonucleotide that is attached to a polynucleotide and is used to identify and/or track the polynucleotide in a reaction. In some embodiments, a molecular tag is attached to the 3'- or 5'-end of a polynucleotide to form a linear conjugate. In some embodiments, a barcode is appended to a target polynucleotide sequence via a primer extension reaction in which a barcoded primer is used to amplify a target polynucleotide. Barcodes may vary widely in size and composition. In some embodiments, barcodes can each have a length within a range of from 2 to 36 nucleotides, or from 4 to 30 nucleotides, or from 8 to 20 nucleotides. In some embodiments, barcodes are selected from defined sets, or repertoires. In some cases, the nucleotide sequences of barcodes in a defined set may all be unique. That is, each barcode sequence in the set is not identical to any other barcode sequence in the same defined set. A plurality of target polynucleotides, when barcoded with a defined set having unique barcode sequences, may be distinctly barcoded. In some cases, the nucleotide sequences of barcodes in a defined set may not be unique, that is, an individual barcode sequence may be identical to another individual barcode sequence in the same defined set. In some embodiments, barcodes are selected from random sequence oligonucleotides of a predetermined length.

"Sequence variant" refers to any variation in sequence relative to one or more reference sequences. Typically, the sequence variant occurs with a lower frequency than the reference sequence for a given population of individuals for whom the reference sequence is known. In some cases, the reference sequence is a single known reference sequence, such as the genomic sequence of a single individual. In some cases, the reference sequence is a consensus sequence formed by aligning multiple known sequences, such as the genomic sequence of multiple individuals serving as a reference population, or multiple sequencing reads of polynucleotides from the same individual. In some cases, the sequence variant occurs with a low frequency in the population (also referred to as a "rare" sequence variant). For example, the sequence variant may occur with a frequency of about or less than about 5%, 4%, 3%, 2%, 1.5%, 1%, 0.75%, 0.5%, 0.25%, 0.1%, 0.075%, 0.05%, 0.04%, 0.03%, 0.02%, 0.01%, 0.005%, 0.001%, or lower. In some cases, the sequence variant occurs with a frequency of about or less than about 0.1%. A sequence variant can be any variation with respect to a reference sequence. A sequence variation may consist of a change in, insertion of, or deletion of a single nucleotide, or of a plurality of nucleotides (e.g. 2, 3, 4, 5, 6, 7, 8, 9, 10, or more nucleotides). Where a sequence variant comprises two or more nucleotide differences, the nucleotides that are different may be contiguous with one another, or discontinuous. Non-limiting examples of types of sequence variants include single nucleotide polymorphisms (SNP), deletion/insertion polymorphisms (DIP), copy number variants (CNV), short tandem repeats (STR), simple sequence repeats (SSR), variable number of tandem repeats (VNTR), amplified fragment length polymorphisms (AFLP), retrotransposon-based insertion polymorphisms, sequence specific amplified polymorphism, and differences in epigenetic marks that can be detected as sequence variants (e.g. methylation differences). In some embodiments, a sequence variant can refer to a chromosome rearrangement, including but not limited to a translocation or fusion gene.

In an aspect, the present disclosure provides methods for accurately determining sequence variants, e.g., rare sequence variants, by combining sequence information from complementary strands (e.g., sense and antisense strands) of target polynucleotides. In some embodiments, complementary strands of a target, double-stranded polynucleotide are asymmetrically barcoded and derivatives (e.g., amplification products) of complementary strands of a target, double-stranded polynucleotide are rendered separately identifiable by barcode sequences.

In some embodiments, two strands are identified as originating from the same double-stranded polynucleotide in a sample based on polynucleotide sequences and strand identifying barcodes. In some embodiments, two strands are identified as originating from the same double-stranded polynucleotide in a sample based on complementary junction sequences formed from linking 5' and 3' polynucleotide ends (e.g., after circularizing). In accordance with some embodiments, the junction sequences formed by linking 5' and 3' polynucleotide ends identified in sequencing data can be used identify sequencing reads as originating from a particular double-stranded input, or starting, molecule. Strand identifying barcodes can be used to distinguish sequencing reads as originating from a particular strand of a pair of complementary strands. In additional embodiments, amplification and sequencing errors may be reduced by unique auxiliary barcodes useful in identifying unique amplicons derived from individual strands of a pair of complementary strands.

In an aspect, the present disclosure provides a method of identifying complementary strands of a double-stranded polynucleotide. The method comprises subjecting a sense strand circular polynucleotide and an antisense strand circular polynucleotide originating from a common double-stranded polynucleotide to a rolling circle amplification reaction using a sense strand primer and an antisense strand primer. The sense strand primer can comprise a sense strand identifying barcode, and the antisense strand primer can comprise an anti sense strand identifying barcode. The rolling circle amplification reaction can yield barcoded concatemers, individual barcoded concatemers comprising a junction sequence formed at a circularization junction of the sense strand circular polynucleotide or the antisense strand circular polynucleotide and multiple repeats of the circular polynucleotide sequence. Next, the barcoded concatemers can be subjected to a primer extension reaction using a first set and a second set of auxiliary primers to generate a plurality of amplicons. The first set of auxiliary primers can hybridize to a barcoded concatemer of the sense strand, and the second set of auxiliary primers can hybridize to a barcoded concatemer of the anti-sense strand. Individual primers of the first set and the second set of auxiliary primers can be distinctly barcoded with respect to other members of the same set. Individual amplicons generated can be distinguishable from each other by a unique combination of (i) the strand identifying barcode at one end (e.g., sense strand identifying barcode, antisense strand identifying barcode), and (ii) a distinct auxiliary barcode at the other end. The amplicons or derivatives thereof can then be sequenced to produce sequencing reads. The sense strand and anti sense strand can be identified as complementary strands of the common double-stranded polynucleotide from the sequencing reads based on junction sequence and the strand identifying barcode (e.g., sense strand identifying barcode, antisense strand identifying barcode). In some cases, unique amplicons of the sense strand and antisense strand can be identified can be identified based on a unique combination of the strand identifying barcode and auxiliary barcode.

The sense strand primer and antisense strand primers for conducting rolling circle amplification can comprise strand identifying barcodes useful in distinguishing barcoded concatemers of the sense strand from barcoded concatemers of the antisense strand. Barcoded concatemers can comprise at least one repeat, or at least one copy, of either the sense strand sequence or the antisense strand sequence. A barcoded concatemer comprising a copy of the sense strand can comprise the antisense strand sequence, but, for simplicity, will be referred to herein as comprising a copy of the sense strand. Similarly, a barcoded concatemer comprising a copy of the antisense strand can comprise the sense strand sequence, but, for simplicity, will be referred to herein as comprising a copy of the antisense strand. In some embodiments, rolling circle amplification may be followed by amplification via polymerase chain reaction (PCR) to yield additional nucleic acid product. While further amplification may generate additional copies of barcoded concatemers, nucleic acid products originating from the sense strand can be identified by the presence of the sense strand barcode. Similarly, nucleic acid products originating from the anti-sense strand can be identified by the presence of the anti-sense strand barcode.

The sense strand primer can comprise a sequence complementary to the sense strand circular polynucleotide. Similarly, the anti-sense strand primer can comprise a sequence complementary to the antisense strand circular polynucleotide. The sequences complementary to the sense strand or antisense strand may comprise specific sequences, e.g., gene specific sequences, and can hybridize to their respective circular polynucleotides. In some embodiments, the sequence capable of hybridizing to the circular polynucleotide is located at the 3' end of the primer. The strand identifying barcode can be located at the 5' end of the primer. The barcode sequence can be located at the 5' end of the resulting concatemer. Sense strand primers and antisense strand primers, in various embodiments herein, may further comprise additional sequence elements. For example, the sense strand primer and/or anti sense strand primer may comprise one or more amplification primer annealing sequences or complements thereof; one or more sequencing primer annealing sequences or complements thereof; one or more barcode sequences; one or more common sequences shared among multiple different primers; one or more restriction enzyme recognition sites; one or more probe binding sites or sequencing adapters (e.g., for attachment to a sequencing platform, such as a flow cell for massive parallel sequencing); one or more random or near-random sequences (e.g. one or more nucleotides selected at random from a set of two or more different nucleotides at one or more positions, with each of the different nucleotides selected at one or more positions represented in a pool of primers comprising the random sequence); and combinations thereof.

A set of auxiliary primers, in embodiments herein, refers to a set of barcoded primers useful in generating amplicons from barcoded concatemers. Individual primers of a set of auxiliary primers may be distinctly barcoded with respect to other members of the same set. For example, individual primers of a set of auxiliary primers may comprise the same primer sequence, or the sequence which hybridizes to the concatemer and initiates primer extension, but comprise barcodes that are distinct from other primers in the same set.

A first set and second set of auxiliary primers can be used with the barcoded concatemers in primer extension to generate a plurality of amplicons which are distinctly barcoded. The first set of auxiliary primers can hybridize to a barcoded concatemer of the sense strand, while the second set of auxiliary primers can hybridize to a barcoded concatemer of the antisense strand. When individual primers of the first set of auxiliary primers are distinctly barcoded with respect to other members of the first set, unique amplicons resulting from the primer extension using the first set of auxiliary primers can comprise the same repeat sequence, the same junction sequence, and the same strand identifying barcode but different auxiliary barcodes. When individual primers of the second set of auxiliary primers are distinctly barcoded with respect to other members of the second set, unique amplicons resulting from the primer extension using the second set of auxiliary primers can comprise the same repeat sequence, the same junction sequence, and the same strand identifying barcode but different auxiliary barcodes. In some cases, the second primer extension reaction comprises polymerase chain reaction, isothermal amplification, or a combination thereof.

Primers of the first set of auxiliary primers can comprise a sequence complementary to a barcoded concatemer of the sense strand. Similarly, primers of the second set of auxiliary primers can comprise a sequence complementary to a barcoded concatemer of the antisense strand. The sequences complementary to barcoded concatemers of the sense strand or antisense strand may comprise specific sequences, e.g., gene specific sequences, and can hybridize to their respective barcoded concatemers. In some embodiments, the sequence capable of hybridizing to the concatemer is located at the 3' end of the primer. The auxiliary barcode can be located at the 5' end of the primer. The auxiliary barcode sequence can be located at the 5' end of the resulting amplicon. Auxiliary primers, in various embodiments herein, may further comprise additional sequence elements. For example, auxiliary primers may comprise one or more amplification primer annealing sequences or complements thereof; one or more sequencing primer annealing sequences or complements thereof; one or more barcode sequences; one or more common sequences shared among multiple different primers; one or more restriction enzyme recognition sites; one or more probe binding sites or sequencing adapters (e.g., for attachment to a sequencing platform, such as a flow cell for massive parallel sequencing); one or more random or near-random sequences (e.g. one or more nucleotides selected at random from a set of two or more different nucleotides at one or more positions, with each of the different nucleotides selected at one or more positions represented in a pool of primers comprising the random sequence); and combinations thereof.

Amplicons resulting from the primer extension reaction can comprise barcodes at both the 5' end and the 3' end of the amplicon. The auxiliary barcode can be found at the 5' end of the molecule. A reverse complement of the strand identifying barcode can be found at the 3' end of the molecule. In cases where individual primers of the first set and the second set of auxiliary primers are distinctly barcoded with respect to other members of the set, the resulting amplicons derived from the sense strand or antisense strand can comprise a unique auxiliary barcode but the same strand identifying barcode for the respective sense strand and antisense strand.

The amplicons, or derivatives thereof, can then be sequenced to produce sequencing reads. In some cases, amplicons can be directly sequenced. In some cases, the amplicons are subject to additional preparation steps to yield derivatives, and the derivatives are sequenced. In some embodiments, amplicons are converted to double-stranded form by complementary strand synthesis. The complementary strand can be synthesized by providing one or more primers that each anneal to a specific site of the amplicon and extending the one or more primers by a polymerase. In some embodiments, adaptor sequences (e.g., flow cell adaptor sequences, sequencing adaptor sequences) are attached to the amplicons or derivatives thereof prior to sequencing. In some cases, sequencing primer binding sites are attached, e.g., via adaptor ligation, PCR, or the like, to prepare amplicons for particular sequencing techniques.

The resulting sequencing reads can comprise a strand identifying barcode, an auxiliary barcode, a concatemer comprising at least one repeat of a sense strand or antisense strand sequence, and a junction sequence formed by a circularization junction. Sequencing reads originating from a common double-stranded polynucleotide can be identified based on repeat sequence and junction sequence. Amongst reads originating from a given double-stranded polynucleotide, reads from a sense strand can be identified based on the presence of the sense strand barcode. Similarly, reads originating from an antisense strand can be identified based on the presence of the antisense strand barcode. Amongst reads originating from the sense strand, those originating from a given amplicon can be identified based on a unique auxiliary barcode. Amongst reads originating from the antisense strand, those originating from a given amplicon can also be identified based on a unique auxiliary barcode. In some cases, sequencing reads of a given amplicon can be grouped into an amplicon family.

Figure 1B:
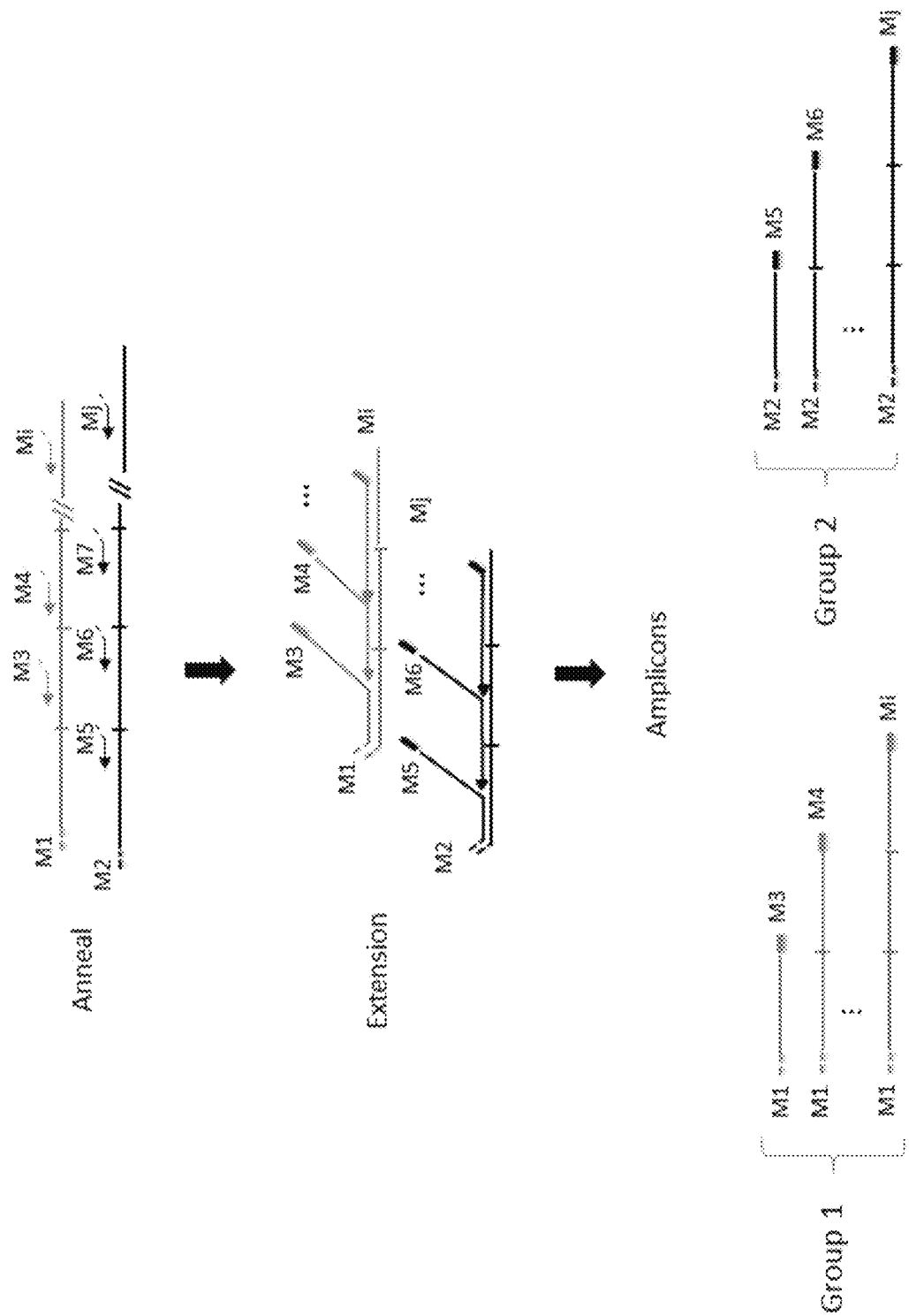

FIGS. 1A and 1B illustrate an example of generating amplicons. As shown in FIG. 1A, a sense strand primer comprising a sense strand identifying barcode (M1) and an antisense strand primer comprising an antisense strand identifying barcode (M2), anneal to a sense strand circular polynucleotide and an antisense strand circular polynucleotide. The sense strand circular polynucleotide and the antisense strand circular polynucleotide comprise complementary junction sequences 1001 and 1002. Rolling circle amplification results in barcoded linear concatemers having at least one repeat of the circular polynucleotide sequence (e.g., the sense strand sequence or the antisense strand sequence). Next, as shown in FIG. 1B, a first set of auxiliary primers and a second set of auxiliary primers anneal to the barcoded linear concatemers. Individual primers of the first set of auxiliary primers are distinctly barcoded with respect to other members of the first set (e.g., M3, M4, . . . Mi). Individual primers of the second set of auxiliary primers are distinctly barcoded with respect to other members of the second set (e.g., M5, M6, . . . Mj). Primer extension results in amplicons barcoded at both 5' and 3' ends. Amplicons of the same barcoded linear concatemer can have either a sequence complementary to the sense strand identifying barcode or the antisense strand identifying barcode at one end of the molecule (e.g., M1 or M2) and unique auxiliary barcode sequences at the other end of the molecule (e.g., M3, M4, . . . Mi of Group 1; M5, M6, . . . Mj of Group 2).

Figure 2:
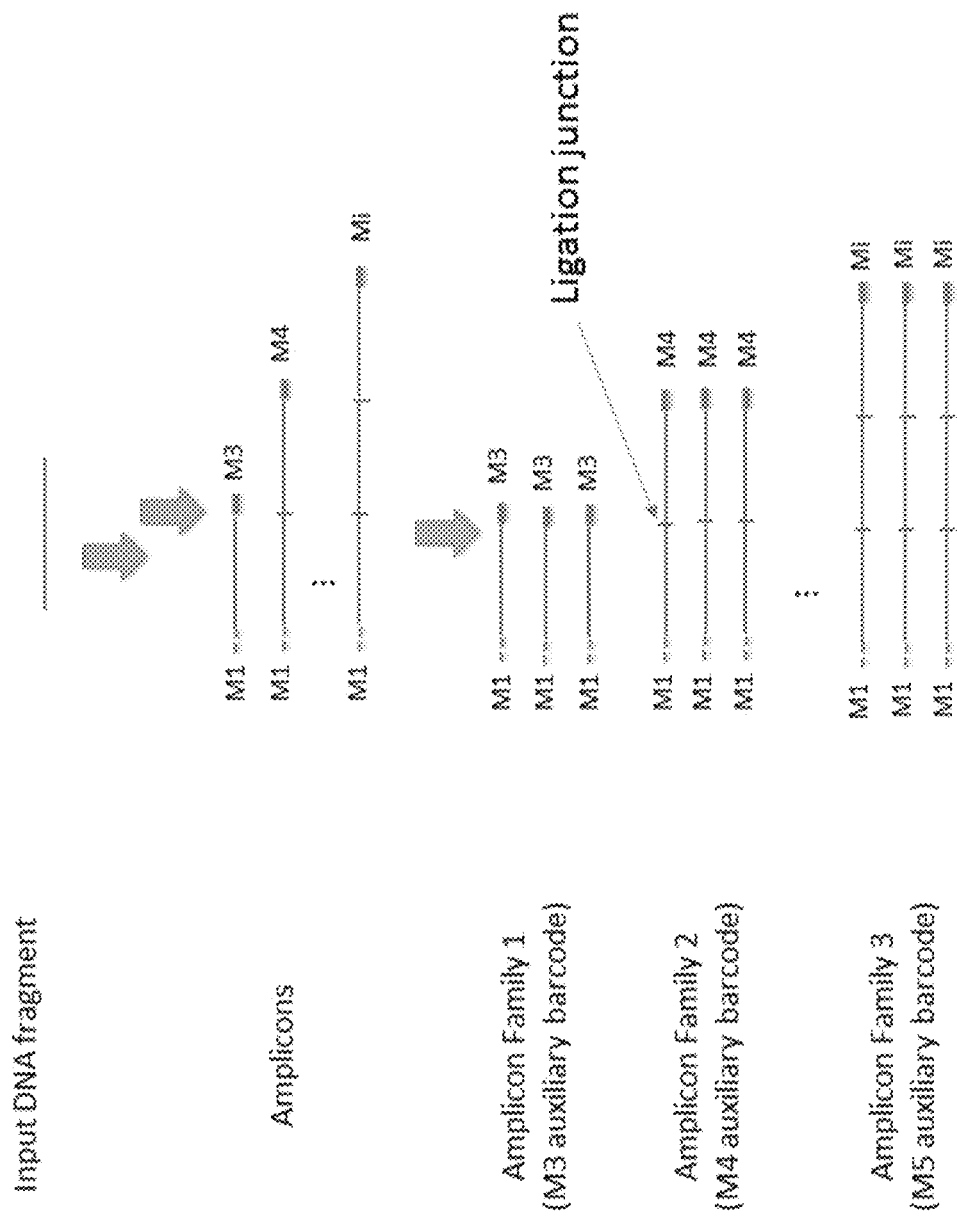
FIG. 2 illustrates amplicon families.

FIG. 2 provides an example of amplicon families. Implementing the methods described herein yields a plurality of amplicons barcoded at both the 5' end and the 3' end of the amplicon. Sequencing reads obtained from sequencing the amplicons, or derivatives thereof, can comprise a strand identifying barcode (e.g., M1), an auxiliary barcode (e.g., M3, M4, or Mi), at least one repeat of the input DNA sequence, and a junction sequence formed by the ligation junction. Sequencing reads originating from a common amplicon can be identified based on a unique auxiliary barcode sequence (e.g., M3, M4, or Mi). The sequencing reads corresponding to a given amplicon can be grouped into an amplicon family (e.g., amplicon family 1, family 2, family 3).

Various methods can be used to identify the repeat sequence of a concatemer in a sequencing read. The junction sequence can be identified by reconstructing the junction via alignment of the repeat sequence to a reference sequence. Concatemers having the same repeat sequence and the same junction sequence can be identified as originating from amplicons of the same input molecule or a common double-stranded polynucleotide. Concatemers identified as originating from the same input molecule can be further distinguished as originating from the sense strand or the antisense strand based on the strand identifying barcode. In some embodiments, the sense strand and the antisense strand are identified based on the repeat sequence, the junction sequence, and the strand identifying barcode. In some embodiments, amplicons of the sense strand and antisense strand are identified based on the junction sequence and the unique combination of (i) the strand identifying barcode at one end and (ii) the distinct auxiliary barcode at the other end.

In an aspect, the present disclosure provides a method for identifying a sequence variant in a polynucleotide relative to a reference sequence. In some embodiments, the method comprises subjecting a sense strand circular polynucleotide and an antisense strand circular polynucleotide originating from a double-stranded polynucleotide to a rolling circle amplification reaction using a sense strand primer and an antisense strand primer. The sense strand primer can comprise a sense strand identifying barcode and the antisense strand primer can comprise an antisense strand identifying barcode. The rolling circle amplification reaction can yield barcoded concatemers, each comprising a junction sequence formed at a circularization junction of a sense strand circular polynucleotide or an antisense strand circular polynucleotide and multiple repeats of the circular polynucleotide sequence. The barcoded concatemers can be subjected to a primer extension reaction using a first set and a second set of auxiliary primers to generate amplicons. The first set of auxiliary primers can hybridize to a barcoded concatemer of the sense strand, and the second set of auxiliary primers can hybridize to a barcoded concatemer of the anti sense strand. Individual primers of the first set and the second set of auxiliary primers may be distinctly barcoded with respect to other members of the same set. Individual amplicons generated can be distinguishable from each other by a unique combination of (i) the strand identifying barcode at one end and (ii) a distinct auxiliary barcode at the other end. The amplicons or derivatives thereof can be sequenced to produce sequencing reads. In some embodiments, a sequence difference in a polynucleotide can be called as a sequence variant relative to a reference sequence when the sequence difference occurs in (i) sequencing reads sharing the same junction sequence, (ii) sequencing reads having different strand identifying barcodes, and (iii) sequencing reads having the same strand identifying barcode but different auxiliary barcodes. In some embodiments, a sequence difference in a sense strand or an antisense strand relative to a reference sequence can be called as a sequence variant when the sequence difference occurs in (i) sequencing reads having a different junction sequence and (ii) sequencing reads having different auxiliary barcodes.

A sequence difference can be called a sequence variant relative to a reference sequence when the sequence difference occurs in both the sense strand and antisense strand of a common double-stranded input molecule. In some embodiments, a sequence difference can be called as a sequence variant relative to a reference sequence when the sequence difference occurs in (i) sequencing reads sharing the same junction sequence, (ii) sequence reads having different strand-identifying barcodes, and (iii) sequence reads having the same strand identifying barcodes but different auxiliary barcodes.

As discussed in embodiments elsewhere herein, sequencing reads can comprise a strand identifying barcode, an auxiliary barcode, at least one repeat of a sense strand or antisense strand sequence, and a junction sequence. Sequencing reads originating from a common double-stranded polynucleotide can be identified based on repeat sequence and junction sequence at a circularization junction. Amongst reads originating from a common double-stranded polynucleotide, those originating from a sense strand can be identified based on the presence of the sense strand barcode. Similarly, those originating from an antisense strand can be identified based on the presence of the antisense strand barcode. Amongst reads of molecules originating from the sense strand, those originating from a given amplicon can be identified based on a unique auxiliary barcode. Amongst reads originating from the antisense strand, those originating from a given amplicon can also be identified based on a unique auxiliary barcode. In some cases, sequencing reads of a given amplicon are grouped into an amplicon family.

A sequence difference can be identified in a repeat of a concatemer of a sequencing read when compared to a reference sequence. A sequence difference identified in a repeat of a concatemer compared to a reference sequence may indicate the presence of a mutation in the input polynucleotide or a processing error, for example during rolling circle amplification, primer extension, and/or sequencing.

In some cases, the sequence difference occurs in all repeats of the concatemer of a given sequencing read. A sequence difference that occurs in all repeats of the concatemer may indicate the presence of a mutation in the input polynucleotide. In some cases, the sequence difference may not occur in all repeats of the concatemer of a given sequencing read. A sequence difference that does not occur in all repeats of the concatemer may indicate that an error occurred, for example, during rolling circle amplification, primer extension, and/or sequencing.

In some embodiments, a given sequencing read is identified as having the sequence difference when the sequence difference occurs in at least 50% of repeats of the concatemer of the given sequencing read. In some cases, the given sequencing read is identified as having the sequence difference when the sequence difference occurs in at least 55%, 60%, 65%, 70%, 75%, 80%, 85%, 90%, or 95% of repeats of the concatemer of the given sequencing read. The given sequencing read may be identified as having the sequence difference when the sequence difference occurs in all repeats of the concatemer of the given sequencing read.

In some embodiments, a given amplicon family is identified as having the sequence difference when the sequence difference occurs in at least 50% of sequencing reads in the amplicon family. In some cases, the given amplicon family is identified as having the sequence difference when the sequence difference occurs in at least 55%, 60%, 65%, 70%, 75%, 80%, 85%, 90%, or 95% of sequencing reads of the given amplicon family. The given amplicon family may be identified as having the sequence difference when the sequence difference occurs in all sequencing reads of the amplicon family. An amplicon family, as described elsewhere herein, comprises sequencing reads originating from a common amplicon. Sequencing reads of a common amplicon can be identified, for example, based on a unique auxiliary barcode sequence, the strand identifying sequence, repeat sequence, and junction sequence.

In some embodiments, a sense strand or an antisense strand is identified as having the sequence difference relative to a reference sequence when the sequence difference occurs in at least 50% of amplicon families corresponding to the sense strand or the antisense strand. In some cases, the sense strand or antisense strand is identified as having the sequence difference relative to a reference sequence when the sequence difference occurs in at least 55%, 60%, 65%, 70%, 75%, 80%, 85%, 90%, or 95% of amplicon families corresponding to the sense strand or the antisense strand. The sense strand or anti sense strand may be identified as having the sequence difference when the sequence difference occurs in all amplicon families corresponding to the sense strand or the antisense strand. The sequence difference can be called as the sequence variant relative to the reference sequence when the sequence difference is confirmed in at least two amplicon families (e.g., at east 3, 4, 5, 6, 7, 8, 9, 10, or more amplicon families) of the sense strand and/or antisense strand. The amplicon families corresponding to a given sense strand or antisense strand, as described elsewhere herein, comprises the amplicon families originating from the given sense strand or antisense strand.

Sequencing reads sharing the same junction sequence can originate from a common double-stranded input molecule. Sequencing reads sharing the same junction sequence and different strand identifying barcodes can indicate reads of both sense and antisense strands of a common double-stranded input molecule. Sequence reads having the same strand identifying barcode but different auxiliary barcodes can indicate different amplicons of the same strand.

Figures 3A, 3B:
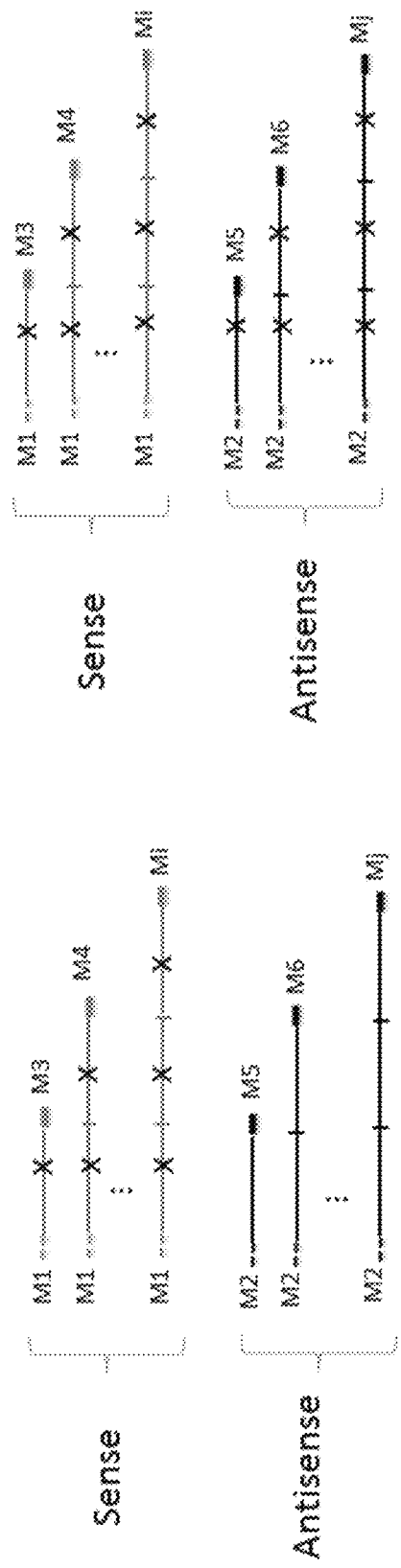
FIGS. 3A and 3B illustrate an example of variant confirmation.

After identification of pairs of concatemers containing complementary strands, concatemer sequences may be aligned and base calls at matching positions of the two strands may be compared. At some positions of concatemer pairs, a base called at a given position in one member of a pair may not be complementary to the base called on the other member of the pair, indicating that an incorrect call has been made due to, for example, amplification error, sequencing error, or the like. FIGS. 3A and 3B illustrate an example. As shown in FIG. 3A, a base call 'X' at a given position in a sense strand may not be complementary to the base called on the antisense strand of the pair. The variant 'X' is not reported as a variant since the variant is not confirmed by both strands. The variant 'X' may be reported as a variant when confirmed by both strands. For example, as shown in FIG. 3B, a base call 'X' at a given position in a sense strand is complementary to the base called on the antisense strands of the pair.

In some cases, where bases at a specified position in complementary strands originating from the same double-stranded molecule (e.g. as identified by the complementary junction sequences and repeat sequences) are not complementary, a base call may be resolved in favor of the reference sequence to which the sample sequence is compared, such that the difference is not identified as a true sequence variant with respect to such reference sequence.

Figures 4A, 4B:
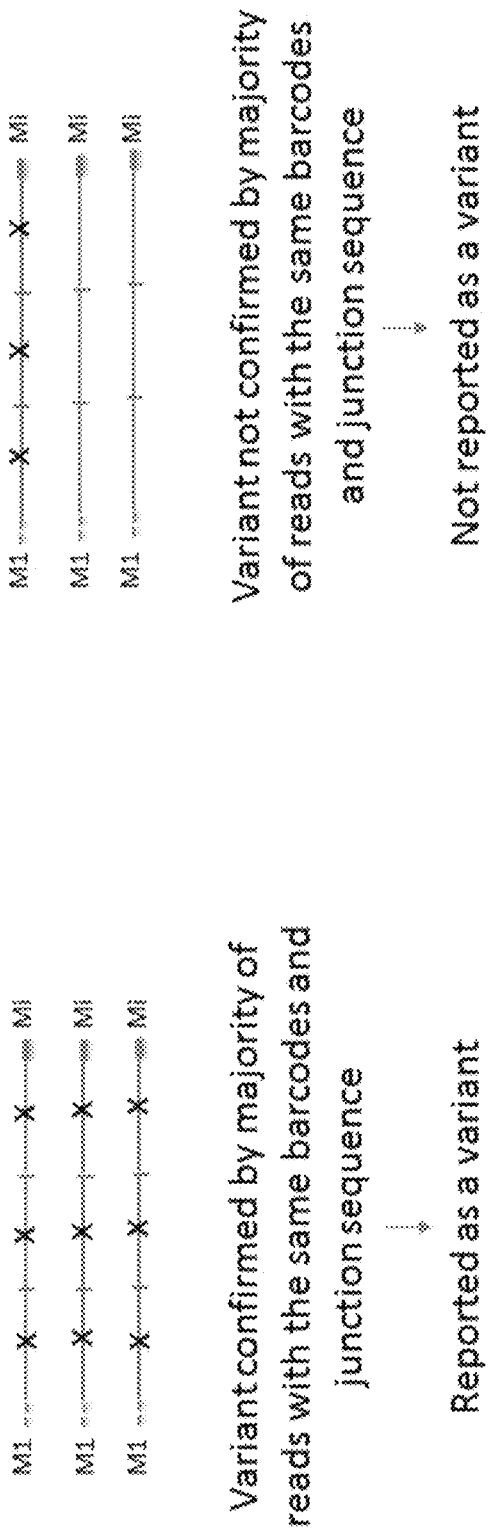
FIGS. 4A and 4B illustrate an example of variant confirmation.

In some cases, indeterminacy of a base call at a given position within an amplicon family may be resolved by examining the base calls at corresponding positions of repeats of other reads in the family. FIGS. 4A and 4B illustrate an example. As shown in FIG. 4A, a base call 'X' at a given position is confirmed by all reads with the same barcode sequences and junction sequence. The variant 'X' is reported as a variant for the amplicon family. The variant 'X' may not be reported for the amplicon family if the variant is not confirmed by a majority of reads. For example, as shown in FIG. 4B, a base call 'X' may be confirmed by all repeats of a concatemer for a given sequencing read. However, the base call 'X' is not confirmed by a majority of reads with the same barcode sequences and junction sequence, and therefore the base call 'X' is not reported as a variant.

Variants found in both concatemers identified as sense and antisense strands of a common double-stranded input molecule may have a higher statistical confidence level, which can be used to perform error correction. Variant confirmation using strand identity may be carried out by (but is not limited to) the following steps: a) variants found in reads corresponding to sense and antisense strands of a common input molecule are considered more confident; b) reads carrying variants can be grouped by its junction identification, the variants are more confident when sense and antisense strands are found in reads within a group of reads having the same junction identification; c) reads carrying variants can be grouped by their molecular barcodes or the combination of molecular barcodes and junction identifications.

Error correction using molecular barcodes and junction identification can be used independently, or combined with the error correction with concatemer sequencing. Error correction techniques may include a) grouping reads with different junction identifications into different read families which represent reads originating from different input molecules, b) building consensus sequences from the families of reads, c) using consensus sequences for variant calling, and d) combining barcodes and junction identifications to form a composite identification (ID) for reads, which can be used to identify the original input molecules. In some embodiments, a base call (e.g. a sequence difference with respect to a reference sequence) found in different read families are assigned a higher confidence. In some cases, a sequence difference is only identified as a true sequence variant representative of the original source polynucleotide (as opposed to an error of sample processing or analysis) if the sequence difference passes one or more filters that increase confidence of a base call. In some embodiments, a sequence difference is only identified as a true sequence variant if (a) it is identified on both strands of a double-stranded input molecule; (b) it occurs in the consensus sequence for the concatemer from which it originates (e.g. more than 50%, 60%, 70%, 80%, 90% or more of the repeats within the concatemer contain the sequence difference); and/or (c) it occurs in two different molecules (e.g. as identified by different junction sequences).

In some cases, a pair of sense and anti sense strands originating from a common double-stranded input molecule may not be identified. The sequence difference in an unpaired sense strand or antisense strand can be called a sequence variant when the sequence difference occurs in the sense strand or antisense strand of an additional double-stranded input molecule. Sequencing reads of an additional double-stranded input molecule can be identified based on junction sequence. For example, the additional double-stranded input molecule can comprise a junction sequence different from that of the unpaired sense strand or antisense strand. The sense strand or antisense strand of the additional double-stranded input molecule can be identified as having the sequence difference relative to a reference sequence when the sequence difference occurs in at least 50% of amplicon families (e.g., 55%, 60%, 65%, 70%, 75%, 80%, 85%, 90%, or 95% of amplicon families) corresponding to the sense strand or the antisense strand of the additional input molecule. An amplicon family corresponding to the sense strand or antisense strand of the additional input molecule can be identified as having the sequence difference when the sequence difference occurs in at least 50% of sequencing reads (e.g., at least 55%, 60%, 65%, 70%, 75%, 80%, 85%, 90%, or 95% of sequencing reads) of the amplicon family. An amplicon family of the sense strand or antisense strand of the additional input molecule can be identified from the repeat sequence, junction sequence, strand identifying barcode, and unique auxiliary barcode. A sequencing read of an amplicon family corresponding to the sense strand or antisense strand of the additional input molecule can be identified as having the sequence difference when the sequence difference occurs in at least 50% of repeats (e.g., at least 55%, 60%, 65%, 70%, 75%, 80%, 85%, 90%, or 95% of repeats) of the concatemer of the sequencing read. A sequence difference in a sense strand or an antisense strand relative to a reference sequence can be called as a sequence variant when the sequence difference occurs in sequencing reads having a different junction sequence. In some embodiments, a sequence difference in a sense strand or an antisense strand relative to a reference sequence can be called a sequence variant when the sequence difference occurs in (i) sequencing reads having a difference junction sequence and (ii) sequencing reads having different auxiliary barcodes.

In an aspect, the present disclosure provides a method of identifying a copy number variation of a genetic locus in a sample. In some embodiments, the method comprises subjecting sense strand circular polynucleotides and antisense strand circular polynucleotides to a rolling circle amplification reaction using sense strand primers and antisense strand primers. The sense strand primers can comprise sense strand identifying barcodes, and the antisense strand primers can comprise antisense strand identifying barcodes. The rolling circle amplification reaction yields barcoded concatemers, each comprising a junction sequence formed at a circularization junction of a circular polynucleotide and multiple repeats of the circular polynucleotide sequence. The barcoded concatemers can then be subjected to a primer extension reaction using a first set and a second set of auxiliary primers to generate amplicons. The first set of auxiliary primers can hybridize to a barcoded concatemer of a sense strand, and the second set of auxiliary primers can hybridize to a barcoded concatemer of an antisense strand. Individual primers of the first set and the second set of auxiliary primers can be distinctly barcoded with respect to other members of the same set. Individual amplicons generated can be distinguishable from each other by a unique combination of (i) the strand identifying barcode at one end and (ii) a distinct auxiliary barcode at the other end. The amplicons or derivatives thereof can then be sequenced to produce sequencing reads. One or more distinct polynucleotides comprising the genetic locus can be identified as originating from distinct single-stranded target polynucleotides via (i) a distinct junction sequence or (ii) the strand identifying barcode. A copy number variation of the genetic locus can be identified when the number of distinct polynucleotides comprising the genetic locus, when compared to a number of distinct polynucleotides comprising a reference region, indicates a copy number variation of the genetic locus.

The number of distinct polynucleotides comprising the genetic locus identified as originating from distinct target polynucleotides can be counted to determine a copy number of the genetic locus in a polynucleotide sample. The polynucleotide sample can also contain polynucleotides comprising a reference region. The number of distinct polynucleotides comprising the reference region can be determined using methods provided herein. A copy number variation of the genetic locus can be identified when the number of distinct polynucleotides comprising the genetic locus, in comparison to the reference region, indicates a copy number variation.

In various embodiments of the aspects herein, double-stranded polynucleotides comprise cell-free polynucleotides. The double-stranded polynucleotides can comprise cell-free DNA, cell-free RNA, or a combination thereof. In some embodiments, the double-stranded polynucleotides comprise circulating tumor DNA, circulating tumor RNA, or a combination thereof.

In various embodiments of the aspects herein, a sense strand circular polynucleotide and an anti-sense strand circular polynucleotide can be generated from a double-stranded polynucleotide by a ligation reaction. The ligation reaction can comprise intramolecular ligation in which a 5' end of the linear polynucleotide is joined to a 3' end of the polynucleotide.

In some embodiments, the sense strand circular polynucleotide and the antisense strand circular polynucleotide are generated by first forming single-stranded polynucleotides (e.g., single-stranded sense strand and single-stranded anti-sense strand) from the double-stranded polynucleotide, and then subjecting the single-stranded polynucleotides to a ligation reaction. Double-stranded polynucleotides can be separated into single-stranded form by various methods, including, but not limited to, thermal denaturation and chemical denaturation. In some embodiments of the aspects herein, a double-stranded polynucleotide is first separated into a single-stranded sense strand and a single-stranded anti-sense strand by thermal denaturation. Following strand separation, the single-stranded polynucleotides can then be circularized by linking the 5' end and the 3' end of individual polynucleotides. Individual single-stranded polynucleotides with a 5' end linked to a 3' end can have junction sequences formed at the circularization junction. A junction sequence refers to the nucleotides comprising the junction where the 5' end and the 3' end are linked and is generally read from a 5' to 3' direction. Junction sequences of two circularized single-stranded polynucleotides comprising a sense strand and an antisense strand originated from a common double-stranded polynucleotide can have complementary junction sequences. In various embodiments herein, junction sequences of a sense strand circular polynucleotide and an antisense strand circular polynucleotide originating from a common double-stranded polynucleotide have complementary junction sequences. A junction sequence can comprise any suitable number of nucleotides, for example at least 2, 3, 4, 5, 6, 7, 8, 9, 10 nucleotides or more so long as complementary junction sequences can be identified. In some cases, however, junction sequences of paired sense and antisense strands may not be complementary, for example, if the double-stranded polynucleotide has staggered or overhanging ends.

In some embodiments of the aspects herein, the sense strand circular polynucleotide and the antisense strand circular polynucleotide are generated by first subjecting the double-stranded polynucleotide to a ligation reaction to yield a double-stranded, circular polynucleotide, and then forming single-stranded, circular polynucleotides from the double-stranded, circular polynucleotide. In some embodiments, the circularized single-stranded polynucleotides are formed by first circularizing double-stranded polynucleotides and then separating circularized, double-stranded polynucleotides into individual single-stranded circles. When circularizing double-stranded polynucleotides, the respective 5' and 3' ends of the sense and anti-sense strands can be linked to form, for each strand, a junction sequence.

Samples of Cell-Free Polynucleotides

In some embodiments, polynucleotides analyzed by methods of the present disclosure are "cell-free" polynucleotides. Any cell-free polynucleotide can be used by embodiments of the present disclosure. Cell-free polynucleotides can be obtained from a subject, such as any animal or living organism. Non-limiting examples of subjects are mammals, such as humans, non-human primates, rodents such as mice and rats, dogs, cats, pigs, sheep, rabbits and others. In some embodiments, a subject is healthy, and cell-free polynucleotides obtained from the subject may not comprise a sequence variant associated with a disease or disorder. In some embodiments, a subject is suspected of having a disease or disorder, and cell-free polynucleotides obtained from the subject may comprise a sequence variant associated with the disease or disorder. In some embodiments, a subject is pregnant, and cell-free polynucleotides obtained from the subject comprise fetal polynucleotides.

Cell-free polynucleotides can be obtained from various non-cellular sources. Non-limiting examples of non-cellular sources from which cell-free polynucleotides can be obtained are serum, plasma, blood, perspiration, saliva, urine, stool, semen, mucosal excretions, spinal fluid, amniotic fluid, and lymph fluid. Various methods for collecting samples of non-cellular sources from which cell-free polynucleotides can be obtained are available. In some embodiments, samples of non-cellular sources from which cell-free polynucleotides can be obtained are obtained from a subject. In some embodiments, samples are obtained by venipuncture. In some embodiments, samples are obtained by aspiration.

Various methods and commercial kits are available for obtaining cell-free polynucleotides, such as cell-free DNA, from a sample. Examples of methods and kits for extracting and isolating cell-free polynucleotides, including cell-free DNA, are phenol/chloroform extraction, phenol/chloroform/isoamyl alcohol (PCI)-glycogen extraction, NaI (sodium iodide) extraction, guanidine-resin extraction, the QIAmp DNA Blood Midi kit with carrier RNA, the ChargeSwitch serum kit, the ZR serum DNA kit, Qiagen Qubit™ dsDNA HS Assay kit, Agilent™ DNA 1000 kit, TruSeq™ Sequencing Library Preparation, and the Puregene DNA purification system Blood Kit.

Cell-free polynucleotides, including cell-free DNA and cell-free RNA, can be extracted and isolated from bodily fluids through a partitioning step in which cell-free polynucleotides are separated from cells and other non-soluble components of the bodily fluid. Examples of partitioning techniques are centrifugation and filtration. In some embodiments, cells are not partitioned from cell-free polynucleotides first, but rather lysed. In some embodiments, the genomic DNA of intact cells is partitioned through selective precipitation. Cell-free polynucleotides, including DNA, may remain soluble and may be separated from insoluble genomic DNA and extracted. According to some procedures, after addition of buffers and other wash steps specific to different kits, DNA may be precipitated using isopropanol precipitation. Further clean up steps may be used such as silica based columns to remove contaminants or salts. General steps may be optimized for specific applications. Non-specific bulk carrier polynucleotides, for example, may be added throughout the reaction to optimize certain aspects of the procedure such as yield.

In some embodiments of the various aspects described herein, a circular polynucleotide is formed from ligating a linear polynucleotide. A circularized polynucleotide formed from a linear polynucleotide can comprise a sequence to be characterized, for example, a rare sequence variant or fusion gene (e.g., target polynucleotide). In some embodiments, a linear target polynucleotide is single-stranded. In other embodiments, a linear target polynucleotide is double-stranded. Non-limiting examples of target polynucleotides include DNA, RNA, cDNA, dsDNA, ssDNA, plasmid DNA, cosmid DNA, chromosomal DNA, genomic DNA, viral DNA, bacterial DNA, mtDNA (mitochondrial DNA), mRNA, rRNA, tRNA, nRNA, siRNA, snRNA, snoRNA, scaRNA, microRNA, dsRNA, ribozyme, riboswitch and viral RNA (e.g., retroviral RNA).

In some embodiments of any of the various aspects disclosed herein, a circular polynucleotide comprises a cell-free polynucleotide, including but not limited to a cell-free DNA or RNA (cfDNA or cfRNA). In some embodiments, a cell-free polynucleotide is a circulating tumor DNA or RNA (ctDNA or ctRNA). In some embodiments, a cell-free polynucleotide comprises fetal DNA or RNA. In some embodiments, cell-free polynucleotides are polynucleotides originating from a cell but not directly obtained from a cellular source, such as a tissue sample. Non-limiting examples of sources from which cell-free polynucleotides may originate are normal cells and tissue, abnormal cells and tissue (e.g., cancerous cells or tissue), fetal cells and tissue, and pathogens. A cell-free polynucleotide present in a non-cellular source can result from cell death (e.g., apoptosis or necrosis) or cell shedding. Sequence analysis of cell-free polynucleotides can be used to characterize the cell or population of cells from which the cell-free DNA is derived, such as tumor cells (e.g. in cancer detection), fetal cells (e.g. in prenatal diagnostics), cells from transplanted tissue (e.g. in early detection of transplant failure), a pathogen (e.g., bacteria or virus), or combinations thereof.

In some embodiments of any of the various aspects disclosed herein, a circular polynucleotide comprises genomic DNA. In some embodiments, a circular polynucleotide is derived from genomic DNA. Genomic DNA can be obtained from a cell sample using various methods and commercially available kits, such as a Qiagen DNeasy Tissue Kit. Genomic DNA can be obtained and purified from a sample using any suitable extraction, isolation, and purification method, examples of which are described elsewhere herein. Other non-limiting examples of extraction techniques include: (1) organic extraction followed by ethanol precipitation, e.g., using a phenol/chloroform organic reagent (Ausubel et al., 1993), with or without the use of an automated nucleic acid extractor, e.g., the Model 341 DNA Extractor available from Applied Biosystems (Foster City, Calif.); (2) stationary phase adsorption methods (U.S. Pat. No. 5,234,809; Walsh et al., 1991); and (3) salt-induced nucleic acid precipitation methods (Miller et al., (1988)), such precipitation methods being typically referred to as "salting-out" methods. Another example of nucleic acid isolation and/or purification includes the use of magnetic particles to which nucleic acids can specifically or non-specifically bind, followed by isolation of the beads using a magnet, and washing and eluting the nucleic acids from the beads (see e.g. U.S. Pat. No. 5,705,628). For example, nucleic acids can be isolated and purified using solid phase reversible immobilization (SPRI) beads (Agencourt AMPure XP). In some embodiments, the above isolation methods may be preceded by an enzyme digestion step to help eliminate unwanted protein from the sample, e.g., digestion with proteinase K, or other like proteases. If desired, RNase inhibitors may be added to the lysis buffer. For certain cell or sample types, it may be desirable to add a protein denaturation/digestion step to the protocol. Purification methods may be directed to isolate DNA, RNA, or both. When both DNA and RNA are isolated together during or subsequent to an extraction procedure, further steps may be employed to purify one or both separately from the other. Sub-fractions of extracted nucleic acids can also be generated, for example, purification by size, sequence, or other physical or chemical characteristic. In addition to an initial nucleic acid isolation step, purification of nucleic acids can be performed after any step in the disclosed methods, such as to remove excess or unwanted reagents, reactants, or products. A variety of methods for determining the amount and/or purity of nucleic acids in a sample are available, such as by absorbance (e.g. absorbance of light at 260 nm, 280 nm, and a ratio of these) and detection of a label (e.g. fluorescent dyes and intercalating agents, such as SYBR green, SYBR blue, DAPI, propidium iodide, Hoechst stain, SYBR gold, and ethidium bromide).

In some embodiments, a circular polynucleotide comprises fragmented cell-free DNA or fragmented genomic DNA. Various methods are available for fragmenting polynucleotides, including but not limited to chemical, enzymatic, and mechanical methods such as sonication, shearing, and contacting with restriction enzymes. In some embodiments, cell-free DNA fragments are approximately uniform in length. In some embodiments, cell-free DNA fragments are not approximately uniform in length. In some embodiments, cell-free DNA fragments have an average length from about 50 to about 1000 nucleotides in length. In some embodiments, cell-free DNA fragments have an average length from about 50 to about 500 nucleotides in length. In some embodiments, cell-free DNA fragments have an average length from about 50 to about 250 nucleotides in length. In some embodiments, cell-free DNA fragments have an average length from about 50 to about 200 nucleotides in length. In some embodiments, cell-free DNA fragments have an average length from about 50 to about 100 nucleotides in length. In some embodiments, genomic DNA is fragmented into polynucleotides of shorter lengths. In some embodiments, genomic DNA fragments are approximately uniform in length. In some embodiments, genomic DNA fragments are not approximately uniform in length. In some embodiments, genomic DNA fragments have an average length from about 50 to about 100 nucleotides in length. In some embodiments, genomic DNA fragments have an average length from about 50 and 250 nucleotides in length. In some embodiments, genomic DNA fragments have an average length from about 50 and 500 nucleotides in length. In some embodiments, genomic DNA fragments have an average length from about 50 and 750 nucleotides in length. In some embodiments, genomic DNA fragments have an average length from about 100 and 1000 nucleotides in length.

The starting amount of polynucleotides in a sample may be small. In some embodiments, the amount of starting polynucleotides is less than 50 ng, such as less than 45 ng, 40 ng, 35 ng, 30 ng, 25 ng, 20 ng, 15 ng, 10 ng, 5 ng, 4 ng, 3 ng, 2 ng, 1 ng, 0.5 ng, 0.1 ng, or less. In some embodiments, the amount of starting polynucleotides is in the range of 0.1-100 ng, such as between 1-75 ng, 5-50 ng, or 10-20 ng. In general, lower starting material increases the importance of increased recovery from various processing steps. Processes that reduce the amount of polynucleotides in a sample for participation in a subsequent reaction decrease the sensitivity with which rare mutations can be detected. For example, methods described by Lou et al. (PNAS, 2013, 110 (49)) are expected to recover only 10-20% of the starting material. For large amounts of starting material (e.g. as purified from lab-cultured bacteria), this may not be a substantial obstacle. However, for samples where the starting material is substantially lower, recovery in this low range can be a substantial obstacle to detection of rare variants. Accordingly, in some embodiments, sample recovery from one step to another in a method of the disclosure e.g. the mass fraction of input into a circularization step available for input into a subsequent amplification step (or sequencing step) is about or more than about 50%, 60%, 75%, 80%, 85%, 90%, 95%, or more. Recovery from a particular step may be close to 100%. Recovery may be with respect to a particular form, such as recovery of circular polynucleotides from an input of non-circular polynucleotides.

Circularizing Polynucleotides

Circular polynucleotides may be formed from linear polynucleotides by various methods. In some embodiments, a single linear polynucleotide is circularized by end-joining. In some embodiments, a first linear polynucleotide is joined to a second linear polynucleotide, and then the un-joined end of the first polynucleotide is joined to the un-joined end of the second polynucleotide to form a circular polynucleotide comprising the first and second polynucleotides. Polynucleotides to be circularized may be single-stranded or double-stranded. Where single-stranded circles are desired, the polynucleotide may be a single-stranded polynucleotide as originally isolated, or may be treated to render the polynucleotide single-stranded (e.g. by denaturation). In some embodiments, a method for circularizing a polynucleotide involves an enzyme, such as use of a ligase (e.g., an RNA ligase or a DNA ligase). Non-limiting examples of enzymes that can be used to ligate a linear target polynucleotide into a circular target polynucleotide are ATP-dependent double-stranded polynucleotide ligases, NAD+ dependent DNA or RNA ligases, and single-strand polynucleotide ligases. Non-limiting examples of ligases are CircLigase I and CircLigase II (Epicentre; Madison, Wis.), *Escherichia coli* DNA ligase, *Thermus filiformis* DNA ligase, Tth DNA ligase, *Thermus scotoductus* DNA ligase (I and II), T3 DNA ligase, T4 DNA ligase, T4 RNA ligase, T7 DNA ligase, Taq ligase, Ampligase (Epicentre® Technologies Corp.), VanC-type ligase, 9° N DNA Ligase, Tsp DNA ligase, DNA ligase I, DNA ligase III, DNA ligase IV, Sso7-T3 DNA ligase, Sso7-T4 DNA ligase, Sso7-T7 DNA ligase, Sso7-Taq DNA ligase, Sso7-*E. coli* DNA ligase, Sso7-Ampligase DNA ligase, and thermostable ligases. Ligase enzymes may be wild-type, mutant isoforms, and genetically engineered variants. Ligation reactions may contain a buffer component, small molecule ligation enhancers, and other reaction components. In some embodiments, the concentration of polynucleotides and enzyme is adjusted to facilitate intermolecular ligation rather than intramolecular ligation. In some embodiments, the reaction temperature and reaction time, or length of the reaction, is adjusted. Reaction temperatures and times can be adjusted as well. In some embodiments, 60° C. is used to facilitate intramolecular circles. In some embodiments, reaction times are between 12-16 hours. Reaction conditions may be those specified by the manufacturer of the selected enzyme. In some embodiments, joining the ends of a polynucleotide to form a circular polynucleotide (either directly to itself or to one or more other polynucleotides, e.g., a circular target polynucleotide comprises two target polynucleotides) produces a junction having a junction sequence. In some embodiments, an exonuclease step can be included to digest any unligated nucleic acids after the circularization reaction. That is, closed circles do not contain a free 5' or 3' end, and thus the introduction of a 5' or 3' exonuclease will not digest the closed circles but will digest the unligated components. This may find particular use in multiplex systems.

After circularization, reaction products may be purified prior to amplification or sequencing to increase the relative concentration or purity of circularized polynucleotides available for participating in subsequent steps (e.g. by isolation of circular polynucleotides or removal of one or more other molecules in the reaction). For example, a circularization reaction or components thereof may be treated to remove single-stranded (non-circularized) polynucleotides, such as by treatment with an exonuclease. As a further example, a circularization reaction or portion thereof may be subjected to size exclusion chromatography, whereby small reagents are retained and discarded, or circularization products are retained and released in a separate volume. A variety of kits for cleaning up ligation reactions are available, such as kits provided by Zymo oligo purification kits made by Zymo Research. In some embodiments, purification comprises treatment to remove or degrade ligase used in the circularization reaction, and/or to purify circularized polynucleotides away from such ligase. In some embodiments, treatment to degrade ligase comprises treatment with a protease, such as proteinase K. Proteinase K treatment may follow manufacturer protocols, or standard protocols (e.g. as provided in Sambrook and Green, Molecular Cloning: A Laboratory Manual, 4th Edition (2012)). Protease treatment may also be followed by extraction and precipitation. In one example, circularized polynucleotides are purified by proteinase K (Qiagen) treatment in the presence of 0.1% SDS and 20 mM EDTA, extracted with 1:1 phenol/chloroform and chloroform, and precipitated with ethanol or isopropanol. In some embodiments, precipitation is in ethanol.

Primer Extension and Amplification

Some embodiments of the present disclosure comprise primer extension and amplification reactions, such as one or more of generating concatemers, generating amplicons, and amplifying a plurality of amplicons. Primer extension reactions can involve changes in temperature (thermocycling) or a constant temperature (isothermal). In some embodiments, primer extension reactions comprise polymerase chain reaction (PCR). PCR typically involves cycling through multiple stages of denaturation, annealing of primer pairs to opposite strands, and primer extension to exponentially increase copy numbers of the target sequence, at least some of these stages generally occurring at different reaction temperatures. Non-limiting examples of PCR amplification techniques are quantitative PCR (qPCR or realtime PCR), reverse transcription PCR (RT-PCR), digital PCR (dPCR or dePCR), target-specific PCR, and quantitative reverse transcription PCR (qRT-PCR). For example, in a conventional PCR using Taq DNA polymerase, a double stranded target nucleic acid may be denatured at a temperature >90° C., primers annealed at a temperature in the range 50-75° C., and primers extended at a temperature in the range 72-78° C. Reaction volumes typically range from a few hundred nanoliters, e.g. 200 nL, to a few hundred µL, e.g. 200 µL. Examples of polymerase enzymes that can be used for PCR are thermostable polymerases, including but not limited to, *Thermus thermophilus* HB8; mutant *Thermus oshimai*; *Thermus scotoductus*; *Thermus thermophilus* 1B21; *Thermus thermophilus* GK24; *Thermus aquaticus* polymerase (AmpliTaq® FS or Taq (G46D; F667Y), Taq (G46D; F667Y; E6811), and Taq (G46D; F667Y; T664N; R660G); *Pyrococcus furiosus* polymerase; *Thermococcus gorgonarius* polymerase; *Pyrococcus* species GB-D polymerase; *Thermococcus* sp. (strain 9° N-7) polymerase; *Bacillus stearothermophilus* polymerase; Tsp polymerase; ThermalAce™ polymerase (Invitrogen); *Thermus flavus* polymerase; *Thermus litoralis* polymerase; *Thermus* Z05 polymerase; delta Z05 polymerase (e.g. delta Z05 Gold DNA polymerase); and mutants, variants, or derivatives thereof. Additional examples of polymerase enzymes that can be used for PCR are non-thermostable polymerases, including, but not limited to DNA polymerase I; mutant DNA polymerase I, including, but not limited to, Klenow fragment and Klenow fragment (3' to 5' exonuclease minus); T4 DNA polymerase; mutant T4 DNA polymerase; T7 DNA polymerase; mutant T7 DNA polymerase; phi29 DNA polymerase; and mutant phi29 DNA polymerase. In some embodiments, a hot start polymerase is used. A hot start polymerase is a modified form of a DNA Polymerase that requires thermal activation. Such a polymerase can be used, for example, to further increase sensitivity, specificity, and yield; and/or to further improve low copy target amplification. Typically, the hot start enzyme is provided in an inactive state. Upon thermal activation the modification or modifier is released, generating active enzyme. A number of hot start polymerases are available from various commercial sources, such as Applied Biosystems; Bio-Rad; eEnzyme LLC; Eppendorf North America; Finnzymes Oy; GeneChoice, Inc.; Invitrogen; Jena Bioscience GmbH; MIDSCI; Minerva Biolabs GmbH; New England Biolabs; Novagen; Promega; QIAGEN; Roche Applied Science; Sigma-Aldrich; Stratagene; Takara Minis Bio; USB Corp.; Yorkshire Bioscience Ltd; and the like.

In some embodiments, primer extension and amplification reactions comprise isothermal reactions. Non-limiting examples of isothermal amplification technologies are ligase chain reaction (LCR) (e.g., U.S. Pat. Nos. 5,494,810 and 5,830,711); transcription mediated amplification (TMA) (e.g., U.S. Pat. Nos. 5,399,491, 5,888,779, 5,705,365, 5,710,029); nucleic acid sequence-based amplification (NASBA) (e.g., Malek et al., U.S. Pat. No. 5,130,238); signal mediated amplification of RNA technology (SMART) (e.g., Wharam et al., Nucleic Acids Res. 2001, 29, e54); strand displacement amplification (SDA) (e.g., U.S. Pat. No. 5,455,166); thermophilic SDA (Spargo et al., Mol Cell Probes 1996, 10:247-256; European Pat. No. 0684315); rolling circle amplification (RCA) (e.g., Lizardi, "Rolling Circle Replication Reporter Systems," U.S. Pat. No. 5,854,033); loop-mediated isothermal amplification of DNA (LAMP) (e.g., Notomi et al., "Process for Synthesizing Nucleic Acid," U.S. Pat. No. 6,410,278); helicase-dependent amplification (HDA) (e.g., U.S. Pat. Appl. US 20040058378); single primer isothermal amplification (SPIA) (e.g., WO2001020035 and U.S. Pat. No. 6,251,639); and circular helicase-dependent amplification (cHDA) (e.g., U.S. patent application U.S. Ser. No. 10/594,095).

In some embodiments, primer extension reactions are effected by polymerases having strand-displacement activity, such as for RCA. In some embodiments, isothermal amplification comprises rolling circle amplification (RCA). A RCA reaction mixture can comprise one or more primers, a polymerase having strand displacement activity, and dNTPs. Strand displacement refers to the ability to displace down-stream DNA during synthesis. Polymerases having strand-displacement activity may have varying degrees of strand displacement activity. In some embodiments, a polymerase may have weak or no strand-displacement activity. In some embodiments, polymerases may have strong strand displacement activity. In some embodiments, polymerases with strand displacement activity may have different levels of strand-displacement activity at different reaction temperatures. In some embodiments, a polymerase may display strand displacement activity at moderate temperatures, e.g., 20° C.-37° C. In some embodiments, a polymerase may display strand displacement activity at elevated temperatures, e.g., 65° C. Reaction temperatures can be adjusted to favor a level of activity of a polymerase having strand-displacement activity. In some embodiments, a reaction temperature is at least 20° C., 25° C., 30° C., 35° C., 40° C., 45° C., 50° C., 55° C., 60° C., 65° C., 70° C., 75° C., 80° C., 85° C., or 90° C. In some embodiments, a reaction temperature is between 20° C. and 80° C. In some embodiments, a reaction temperature is between 20° C. and 70° C. In some embodiments, a reaction temperature is between 20° C. and 60° C. In some embodiments, a reaction temperature is between 20° C. and 50° C. In some embodiments, various reaction temperatures can be cycled through in different stages to increase or decrease the strand displacement activity of a polymerase. Non-limiting examples of polymerases having strand displacement activity include Bst DNA polymerase, large fragment; Bsu DNA polymerase, large fragment; Deep VentR™ DNA polymerase; Deep VentR™ (exo-) DNA polymerase; Klenow fragment (3'-5' exo-); DNA polymerase I, large fragment; M-MuLV reverse transcriptase; phi29 DNA polymerase; VentR® DNA polymerase; and VentR® (exo-) DNA polymerase.

Primers of methods herein can be of any suitable length, such as at least 5, 6, 7, 8, 9, 10, 15, 20, 25, 30, 35, 40, 45, 50, 55, 60, 65, 70, 75, 80, 90, or 100 nucleotides or more than 100 nucleotides, any portion or all of which may be complementary to the corresponding target sequence (e.g. about 5, 10, 15, 20, 25, 30, 35, 40, 45, or 50 nucleotides or more than 50 nucleotides). The length of a primer for primer extension can be within a range of 5 to 100 nucleotides, 10 to 85 nucleotides, 15 to 70 nucleotides, or 20 to 60 nucleotides, any portion or all of which may be complementary to the corresponding target sequence (e.g. about 5, 10, 15, 20, 25, 30, 35, 40, 45, or 50 nucleotides or more than 50 nucleotides).

In some embodiments of any of the various aspects of the disclosure, a primer may comprise one or more portions or segments. For example, a primer may comprise one or more amplification primer annealing sequences or complements thereof; one or more sequencing primer annealing sequences or complements thereof; one or more barcode sequences; one or more common sequences shared among multiple different primers; one or more restriction enzyme recognition sites; one or more probe binding sites or sequencing adapters (e.g., for attachment to a sequencing platform, such as a flow cell for massive parallel sequencing); one or more random or near-random sequences (e.g. one or more nucleotides selected at random from a set of two or more different nucleotides at one or more positions, with each of the different nucleotides selected at one or more positions represented in a pool of primers comprising the random sequence); and combinations thereof.

In some embodiments, a primer comprises a sequencing adapter element (herein also referred to as an "adaptor"), which generally refers to oligonucleotides incorporated at the 5' and/or 3' ends of polynucleotides to facilitate one or more steps of a polynucleotide sequencing reaction. In some embodiments, a sequencing adapter is used to bind a polynucleotide comprising the sequencing adapter to a flow cell for next generation sequencing. Non-limiting examples of next-generation sequencing methods are single-molecule real-time sequencing, ion semiconductor sequencing, pyrosequencing, sequencing by synthesis, sequencing by ligation, and chain termination. Sequencing adapters for flow cell attachment may comprise any suitable sequence compatible with next generation sequencing systems, e.g., 454 Sequencing, Ion Torrent Proton or PGM, and Illumina X10. Non-limiting examples of sequencing adapters for next generation sequencing methods include P5 and P7 adapters suitable for use with Illumina sequencing systems; TruSeq Universal Adapter; and TruSeq Indexed Adapter. In some embodiments, a sequencing adapter can be used to enrich, e.g., via amplification, such as polymerase chain reaction (PCR), for polynucleotides comprising the adapter sequence. Sequencing adapters can further comprise a barcode sequence and/or a sample index sequence.

Concatemers and Sequencing

Concatemers generated as products of amplification reactions, including thermocycling methods, isothermal methods, and combinations of these, can comprise two or more repeats of a target polynucleotide sequence, for example a circular polynucleotide sequence. A concatemer may comprise about 2, 3, 4, 5, 6, 7, 8, 9, 10 or more copies of the target polynucleotide. In some embodiments, concatemers are generated as products of primer extension reactions from a plurality of target polynucleotides, wherein constituents of the plurality are non-uniform in length and comprise a plurality of sequences.

Certain embodiments of the present disclosure comprise sequencing a plurality of amplicons. A variety of sequencing methodologies are available for sequencing the plurality of amplicons. In some embodiments, high-throughput sequencing methodologies are used. Non-limiting examples of sequencing methodologies that can be used include sequencing systems manufactured by Illumina (sequencing systems such as HiSeq® and MiSeq®), Life Technologies (Ion Torrent®, SOLiD®, etc.), Roche's 454 Life Sciences systems, Pacific Biosciences systems, etc. In some embodiments, sequencing comprises use of HiSeq® and MiSeq® systems to produce reads of about or more than about 50, 75, 100, 125, 150, 175, 200, 250, 300 nucleotides or more in length. In some embodiments, sequencing comprises a sequencing-by-synthesis process, where individual nucleotides are identified iteratively, as they are added to the growing primer extension product. Pyrosequencing is an example of a sequence by synthesis process that identifies the incorporation of a nucleotide by assaying the resulting synthesis mixture for the presence of by-products of the sequencing reaction, namely pyrophosphate. In particular, a primer/template/polymerase complex is contacted with a single type of nucleotide. If that nucleotide is incorporated, the polymerization reaction cleaves the nucleoside triphosphate between the $\alpha$ and $\beta$ phosphates of the triphosphate chain, releasing pyrophosphate. The presence of released pyrophosphate is then identified using a chemiluminescent enzyme reporter system that converts the pyrophosphate, with AMP, into ATP, then measures ATP using a luciferase enzyme to produce measurable light signals. Where light is detected, the base is incorporated, where no light is detected, the base is not incorporated. Following appropriate washing steps, the various bases are cyclically contacted with the complex to sequentially identify subsequent bases in the template sequence. See, e.g., U.S. Pat. No. 6,210,891.

In certain embodiments of any of the various aspects of the present disclosure, amplicons are purified prior to sequencing. Amplicons can be purified by various methods. Amplicons may be purified to remove excess or unwanted reagents, reactants, or products. Amplicons may further be purified by size, sequence, or other physical or chemical characteristic. In some embodiments, amplicons may be subjected to size exclusion chromatography, whereby amplicons comprising only one copy of the target polynucleotide and/or small reagents (e.g., primers) are retained and discarded, or amplicons comprising two or more copies of the target polynucleotide are retained and released in a separate volume. In some embodiments, amplicons may be subjected to fragment excision from gels and gel filtration (e.g. to enrich for fragments larger than about 300, 400, 500, or more nucleotides in length); as well as SPRI beads (Agencourt AMPure XP) for size selection by fine-tuning the binding buffer concentration. For example, the use of 0.6× binding buffer during mixing with DNA fragments may be used to preferentially bind DNA fragments larger than about 500 base pairs (bp). In some embodiments, amplification products are treated to filter the resulting amplicons on the basis of size to reduce and/or eliminate the number of monomers in a mixture comprising concatemers. This can be done using any purification technique as described elsewhere herein.

Sequence Variants

In some embodiments, the amplicons or derivatives thereof are sequenced to detect a sequence variant, e.g., inversion, deletion, duplication, translocation, single base changes, and rare somatic mutations, with respect to a reference sequence or in a background of no mutations. In some embodiments, the amplicons or derivatives thereof are sequenced to detect copy number variation at a genetic locus. In some embodiments, the sequence variant and/or copy number variation is correlated with disease. In some embodiments, the sequence variant and/or copy number variation is not correlated with disease.

In general, sequence variants for which there is statistical, biological, and/or functional evidence of association with a disease or trait are referred to as "causal genetic variants." A single causal genetic variant can be associated with more than one disease or trait. In some cases, a causal genetic variant can be associated with a Mendelian trait, a non-Mendelian trait, or both. Causal genetic variants can manifest as variations in a polynucleotide, such 1, 2, 3, 4, 5, 6, 7, 8, 9, 10, 20, 50, or more sequence differences (such as between a polynucleotide comprising the causal genetic variant and a polynucleotide lacking the causal genetic variant at the same relative genomic position). Non-limiting examples of types of causal genetic variants include single nucleotide polymorphisms (SNP), deletion/insertion polymorphisms (DIP), copy number variants (CNV), short tandem repeats (STR), restriction fragment length polymorphisms (RFLP), simple sequence repeats (SSR), variable number of tandem repeats (VNTR), randomly amplified polymorphic DNA (RAPD), amplified fragment length polymorphisms (AFLP), inter-retrotransposon amplified polymorphisms (TRAP), long and short interspersed elements (LINE/SINE), long tandem repeats (LTR), mobile elements, retrotransposon microsatellite amplified polymorphisms, retrotransposon-based insertion polymorphisms, sequence specific amplified polymorphism, and heritable epigenetic modification (for example, DNA methylation). A causal genetic variant may also be a set of closely related causal genetic variants. Some causal genetic variants may exert influence as sequence variations in RNA polynucleotides. At this level, some causal genetic variants are also indicated by the presence or absence of a species of RNA polynucleotides. Also, some causal genetic variants result in sequence variations in protein polypeptides. A number of causal genetic variants have been reported. An example of a causal genetic variant that is a SNP is the Hb S variant of hemoglobin that causes sickle cell anemia. An example of a causal genetic variant that is a DIP is the delta508 mutation of the CFTR gene which causes cystic fibrosis. An example of a causal genetic variant that is a CNV is trisomy 21, which causes Down's syndrome. An example of a causal genetic variant that is an STR is tandem repeat that causes Huntington's disease.

Sequence Analysis and Base Calling

According to some embodiments, a sequence difference between sequencing reads and a reference sequence is called as a genuine sequence variant (e.g. existing in the sample prior to amplification or sequencing, and not a result of either of these processes) if it occurs in both strands of a double-stranded polynucleotide and/or it occurs in at least two different polynucleotides (e.g. originating from two different circular polynucleotides, which can be distinguished as a result of having different junctions). Because sequence variants that are the result of amplification or sequencing errors are unlikely to be duplicated exactly (e.g. position and type) on two different polynucleotides comprising the same target sequence, adding this validation parameter greatly reduces the background of erroneous sequence variants, with a concurrent increase in the sensitivity and accuracy of detecting actual sequence variation in a sample. In some embodiments, a sequence variant having a frequency of about or less than about 5%, 4%, 3%, 2%, 1.5%, 1%, 0.75%, 0.5%, 0.25%, 0.1%, 0.075%, 0.05%, 0.04%, 0.03%, 0.02%, 0.01%, 0.005%, 0.001%, or lower is sufficiently above background to permit an accurate call. In some embodiments, the sequence variant occurs with a frequency of about or less than about 0.1%. In some embodiments, the frequency of a sequence variant is sufficiently above background when such frequency is statistically significantly above the background error rate (e.g. with a p-value of about or less than about 0.05, 0.01, 0.001, 0.0001, or lower). In some embodiments, the frequency of a sequence variant is sufficiently above background when such frequency is about or at least about 2-fold, 3-fold, 4-fold, 5-fold, 6-fold, 7-fold, 8-fold, 9-fold, 10-fold, 25-fold, 50-fold, 100-fold, or more above the background error rate (e.g. at least 5-fold higher). In some embodiments, the background error rate in accurately determining the sequence at a given position is about or less than about 1%, 0.5%, 0.1%, 0.05%, 0.01%, 0.005%, 0.001%, 0.0005%, or lower. In some embodiments, the error rate is lower than 0.001%. In some embodiments, additional or alternative verification steps are used in distinguishing sequence differences that result from sample processing, from true sequence variants. Examples of such validation steps are provided herein, such as with regard to any of the various aspects of the present disclosure, including comparison between differentially tagged complementary strands from a single double-stranded sample molecule.

In some embodiments, identifying a genuine sequence variant (also referred to as "calling" or "making a call") comprises optimally aligning one or more sequencing reads with a reference sequence to identify differences between the two, as well as to identify junctions. In general, alignment involves placing one sequence along another sequence, iteratively introducing gaps along each sequence, scoring how well the two sequences match, and preferably repeating for various positions along the reference. The best-scoring match is deemed to be the alignment and represents an inference about the degree of relationship between the sequences. In some embodiments, a reference sequence to which sequencing reads are compared is a reference genome, such as the genome of a member of the same species as the subject. A reference genome may be complete or incomplete. In some embodiments, a reference genome consists only of regions containing target polynucleotides, such as from a reference genome or from a consensus generated from sequencing reads under analysis.

Typically, the sequencing data is acquired from large scale, parallel sequencing reactions. Many of the next generation high-throughput sequencing systems export data as FASTQ files, although other formats may be used. In some embodiments, sequences are analyzed to identify repeat unit length (e.g. the monomer length), the junction formed by circularization, and any true variation with respect to a reference sequence, typically through sequence alignment. Identifying the repeat unit length can include computing the regions of the repeated units, finding the reference loci of the sequences (e.g. when one or more sequences are particularly targeted for amplification, enrichment, and/or sequencing), the boundaries of each repeated region, and/or the number of repeats within each sequencing read. In some embodiments, a sequence variant may be considered a confirmed, or genuine, variant if it occurs in more than one repeated unit of the same polynucleotide, as the same sequence variation is likewise unlikely to occur at the same position in a repeated target sequence within the same concatemer. The quality score of a sequence may be considered in identifying variants and confirmed variants, for example, the sequence and bases with quality scores lower than a threshold may be filtered out. Sequence analysis can also include analyzing sequence data for both strands of a duplex. As noted above, in some embodiments, an identical variant that appears in the sequences of reads from different polynucleotides from the sample (e.g. circularized polynucleotides having different junctions) is considered a confirmed variant. Other bioinformatics methods can be used to further increase the sensitivity and specificity of the variant calls.

In some embodiments, statistical analyses may be applied to determination of variants (mutations) and quantitate the ratio of the variant in total DNA samples. Total measurement of a particular base can be calculated using the sequencing data. For example, from the alignment results calculated in previous steps, one can calculate the number of "effective reads," that is, number of confirmed reads for each locus. The allele frequency of a variant can be normalized by the effective read count for the locus. The overall noise level, that is the average rate of observed variants across all loci, can be computed. The frequency of a variant and the overall noise level, combined with other factors, can be used to determine the confidence interval of the variant call. Statistical models such as Poisson distributions can be used to assess the confidence interval of the variant calls. The allele frequency of variants can also be used as an indicator of the relative quantity of the variant in the total sample.

Computer Systems

In an aspect, the present disclosure provides systems for designing primers and primer sets for methods provided herein, for example sense strand primers, antisense strand primers, and auxiliary primer sets. The primers may comprise any of the features described herein, in relation to any of the various aspects of the disclosure. In some embodiments, the system comprises (a) a computer configured to receive a customer request to design primers; (b) computer readable medium comprising code that, upon execution by one or more processors, designs at least one of a sense strand primer, an antisense strand primer, and an auxiliary primer set; and (c) a report generator that sends a report to a recipient. The report may contain, for example, primer sequences of the sense strand primer, the antisense strand primer, or the auxiliary primer set In an aspect, the present disclosure provides a computer-readable medium comprising code that, upon execution by one or more processors, implements a method according to any of the methods disclosed herein. For example, the computer-readable medium comprising code may implement a method identifying complementary strands originating from a common double-stranded polynucleotide, a method of identifying a sequence variant, or a method of identifying a copy number variation of a genetic locus as provided in various embodiments of the aspects herein. In some embodiments, the present disclosure provides a system comprising a computer configured to execute said code.

Computer readable medium may take many forms, including but not limited to, a tangible storage medium, a carrier wave medium, or physical transmission medium. Non-volatile storage media include, for example, optical or magnetic disks, such as any of the storage devices in any computer(s) or the like, such as may be used to implement the calculation steps, processing steps, etc. Volatile storage media include dynamic memory, such as main memory of a computer. Tangible transmission media include coaxial cables; copper wire and fiber optics, including the wires that comprise a bus within a computer system. Carrier-wave transmission media can take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer can read programming code and/or data. Many of these forms of computer readable media may be involved in carrying one or more sequences of one or more instructions to a processor for execution.

In some embodiments, a computer comprises one or more processors. Processors may be associated with one or more controllers, calculation units, and/or other units of a computer system, or implanted in firmware as desired. If implemented in software, the routines may be stored in any computer readable memory such as in RAM, ROM, flash memory, a magnetic disk, a laser disk, or other storage medium. Likewise, this software may be delivered to a computing device via any known delivery method including, for example, over a communication channel such as a telephone line, the internet, a wireless connection, etc., or via a transportable medium, such as a computer readable disk, flash drive, etc. The various steps may be implemented as various blocks, operations, tools, modules or techniques which, in turn, may be implemented in hardware, firmware, software, or any combination thereof. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc. In some embodiments, the computer is configured to receive a customer request to design primers or perform a method provided herein. The computer may receive the customer request directly (e.g. by way of an input device such as a keyboard, mouse, or touch screen operated by the customer or a user entering a customer request) or indirectly (e.g. through a wired or wireless connection, including over the internet).

In some embodiments, a system provided herein comprises a report generator that sends a report to a recipient. The report can contain, for example, primer sequences and information regarding variant identification. The report generator may send a report automatically in response to the customer request. Alternatively, the report generator may send a report in response to instructions from an operator. The report may be transmitted to a recipient at a local or remote location using any suitable communication medium. For example, the communication medium can be a network connection, a wireless connection, or an internet connection. A report can be transmitted over such networks or connections (or any other suitable means for transmitting information, including but not limited to mailing a physical report, such as a print-out) for reception and/or for review by a recipient. The recipient can be but is not limited to the customer, or electronic system (e.g. one or more computers, and/or one or more servers). In some embodiments, the report generator sends the report to a recipient's device, such as a personal computer, phone, tablet, or other device. The report may be viewed online, saved on the recipient's device, or printed.

Kits

In an aspect, the present disclosure provides a kit for performing methods provided herein. A kit provided herein is useful, for example, for performing a method identifying complementary strands originating from a common double-stranded polynucleotide, a method of identifying a sequence variant, or a method of identifying a copy number variation of a genetic locus as provided in various embodiments of the aspects herein. A kit of the disclosure can include any combination primers, dNTPs, adaptors, enzymes, buffers, and reagents for generating circular single-stranded polynucleotides (e.g., denaturants, ligase, etc.), performing primer extension reactions, for example rolling circle replication and/or polymerase chain reaction (e.g., primers, dNTPs, polymerase, buffers, etc.), sequencing amplicons or derivatives thereof, and identifying complementary strands.

The invention claimed is:

1. A method of identifying a copy number variation of a genetic locus in a sample, said method comprising:
   (a) subjecting sense strand circular polynucleotides and antisense strand circular polynucleotides to a rolling circle amplification reaction using (i) sense strand primers comprising a sense strand identifying barcode and (ii) antisense strand primers comprising an antisense strand identifying barcode, wherein said rolling circle amplification reaction yields barcoded concatemers, each comprising a junction sequence formed at a circularization junction of a circular polynucleotide and multiple repeats of said circular polynucleotide sequence;
   (b) subjecting said barcoded concatemers to a primer extension reaction using a first set and a second set of auxiliary primers to generate amplicons, wherein the first set of auxiliary primers hybridize to a barcoded concatemer of a sense strand and the second set of auxiliary primers hybridize to a barcoded concatemer of an antisense strand, individual primers of the first and the second set of auxiliary primers are distinctly barcoded with respect to other members of the same set, and wherein individual amplicons generated are distinguishable from each other by a unique combination of (i) the strand identifying barcode at one end and (ii) a distinct auxiliary barcode at the other end;
   (c) sequencing the amplicons or derivatives thereof to produce sequencing reads;
   (d) identifying one or more distinct polynucleotides comprising the genetic locus as originating from distinct single-stranded target polynucleotides via (i) a distinct junction sequence or (ii) the strand identifying barcode; and
   (e) identifying a copy number variation of the genetic locus when the number of distinct polynucleotides comprising the genetic locus, when compared to a number of distinct polynucleotides comprising a reference region, indicates a copy number variation of the genetic locus.

2. The method of claim 1, wherein prior to (d), sequencing reads are grouped into amplicon families, wherein an amplicon family comprises sequencing reads having the same strand identifying barcode, the same auxiliary barcode, and the same junction sequence.

3. The method of claim 1, wherein sense strand circular polynucleotides and antisense strand circular polynucleotides are generated by (i) forming single-stranded polynucleotides from double-stranded polynucleotides, and (ii) subjecting said single-stranded polynucleotides to a ligation reaction.

4. The method of claim 1, wherein sense strand circular polynucleotides and antisense strand circular polynucleotides are generated by (i) subjecting double-stranded polynucleotides to a ligation reaction to yield double-stranded, circular polynucleotides, and (ii) forming single-stranded, circular polynucleotides from said double-stranded, circular polynucleotides.

5. The method of claim 1, wherein barcoded concatemers in (b) comprise two or more repeats of the circular polynucleotide sequence.

6. The method of claim 1, wherein said sense strand primers and/or said anti-sense primers comprise a gene specific sequence.

7. The method of claim 1, wherein primers of said first set and/or said second set of auxiliary primers comprise gene specific sequences.

8. The method of claim 1, wherein said sense strand primer and/or said anti-sense strand primer further comprise a tag sequence, a sequencing primer binding sequence, or both.

9. The method of claim 1, wherein primers of said first set and/or said second set of auxiliary primers further comprise a tag sequence, a sequencing primer binding sequence, or both.

10. The method of claim 1, wherein said copy number variation is correlated with a disease.

11. The method of claim 1, wherein said sample comprises cell-free polynucleotides.

12. The method of claim 1, wherein said sample comprises polynucleotides from tumor cells.

13. The method of claim 1, wherein said sample comprises fragmented genomic DNA.

14. The method of claim 1, wherein said sample comprises less than 50 ng of polynucleotides.

15. The method of claim 1, wherein said barcoded concatemer comprises at least two copies of said circular polynucleotide.

* * * * *